US008655598B2

(12) United States Patent
Torres-Roca et al.

(10) Patent No.: US 8,655,598 B2
(45) Date of Patent: *Feb. 18, 2014

(54) PREDICTIVE RADIOSENSITIVITY NETWORK MODEL

(75) Inventors: Javier F. Torres-Roca, St. Petersburg, FL (US); Steven Eschrich, Lakeland, FL (US)

(73) Assignees: University of South Florida, Tampa, FL (US); H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/037,156

(22) Filed: Feb. 28, 2011

(65) Prior Publication Data

US 2012/0041908 A1 Feb. 16, 2012

Related U.S. Application Data

(63) Continuation of application No. 12/053,796, filed on Mar. 24, 2008, now abandoned.

(60) Provisional application No. 60/896,350, filed on Mar. 22, 2007, provisional application No. 60/896,550, filed on Mar. 23, 2007.

(51) Int. Cl.
*G01N 33/50* (2006.01)
*G01N 33/48* (2006.01)

(52) U.S. Cl.
USPC .......................................................... 702/19

(58) Field of Classification Search
None
See application file for complete search history.

(56) References Cited

U.S. PATENT DOCUMENTS

| 6,100,243 | A | 8/2000 | Frisch | |
|---|---|---|---|---|
| 6,342,217 | B1 | 1/2002 | Link et al. | |
| 8,101,349 | B2 * | 1/2012 | Garcia et al. | 435/6.1 |
| 2002/0128220 | A1 | 9/2002 | Gleave | |
| 2003/0175717 | A1 | 9/2003 | Li et al. | |
| 2005/0123945 | A1 * | 6/2005 | Torres-Roca et al. | 435/6 |
| 2005/0282766 | A1 | 12/2005 | Wu et al. | |
| 2006/0210556 | A1 | 9/2006 | Baldwin et al. | |
| 2009/0023149 | A1 * | 1/2009 | Knudsen | 435/6 |
| 2009/0181384 | A1 * | 7/2009 | Nekarda et al. | 435/6 |
| 2011/0039270 | A1 * | 2/2011 | Cowens et al. | 435/6 |

FOREIGN PATENT DOCUMENTS

WO WO 00/50643 8/2000

OTHER PUBLICATIONS

Shah et al. (Cell Cycle-mediated Drug Resistance an Emerging Concept in Cancer Therapy, Clin Cancer Res Aug. 2001, 7, pp. 2168-2181).*
Voy et al. (Extracting Gene Networks for Low-Dose Radiation Using Graph Theoretical Algorithms, Computational Biology, Jul. 2006, vol. 2, Issue 7, pp. 0757-0768).*
Wang et al., "DNA repair factor XPC is modified by SUMO-1 and ubiquitin following UV irradiation," Nucleic Acids Res. 33:4023-4034 (2005).
International Search Report and Written Opinion; Application No. PCT/US2008/076311; mailed May 19, 2009 (12 pages).
Albert et al., "Error and attack tolerance of complex networks," Nature, 406: 378-382 (2000).
Algan et al., "Management of adenocarcinoma of the esophagus with chemoradiation alone or chemoradiation followed by esophagectomy: results of sequential nonrandomized phase II studies," International journal of radiation oncology, biology, physics, 32:753-761 (1995).
Alizadeh et al., "Distinct types of diffuse large B-cell lymphoma identified by gene expression profiling," Nature, 403:503-511 (2000).
Al-Sarraf et al., "Chemoradiotherapy versus radiotherapy in patients with advanced nasopharyngeal cancer: phase III randomized Intergroup study 0099," J Clin Oncol, 16:1310-1317 (1998).
Al-Sarraf et al., "Progress report of combined chemoradiotherapy versus radiotherapy alone in patients with esophageal cancer: an intergroup study," J Clin Oncol, 15:277-284 (1997).
Beer et al., "Gene-expression profiles predict survival of patients with lung adenocarcinoma," Nat Med, 8:816-824 (2002).
Begg et al., "The value of pretreatment cell kinetic parameters as predictors for radiotherapy outcome in head and neck cancer: a multicenter analysis," Radiother Oncol, 50:13-23 (1999).
Bild et al., "Oncogenic pathway signatures in human cancers as a guide to targeted therapies," Nature, 439:353-357 (2006).
Bjork-Eriksson et al., "Tumor radiosensitivity (SF2) is a prognostic factor for local control in head and neck cancers," (2000) Int J Radiat Oncol Biol Phys, 46(1):13-19 (2000).
Bolla et al., "Improved Survival in Patients with Locally Advanced Prostate Cancer Treated with Radiotherapy and Goserelin," N Engl J Med, 337:295-300 (1997).
Bolla et al., "Long-term results with immediate androgen suppression and external irradiation in patients with locally advanced prostate cancer (an EORTC study): a phase III randomised trial," The Lancet 360:103-108 (2002).
Bossett et al., "Chemotherapy with Preoperative Radiotherapy in Rectal Cancer," N Engl J Med, 355:1114-1123 (2006).
Bourhis et al., "Potential doubling time and clinical outcome in head and neck squamous cell carcinoma treated with 70 GY in 7 weeks," Int J Radiat Oncol Biol Phys, 35:471-476 (1996).
Brizel et al., "Hyperfractionated Irradiation with or without Concurrent Chemotherapy for Locally Advanced Head and Neck Cancer," N Engl J Med, 338:1798-1804 (1998).

(Continued)

*Primary Examiner* — Jason Sims
(74) *Attorney, Agent, or Firm* — Fish & Richardson P.C.

(57) ABSTRACT

This invention is a model that simulates the complexity of biological signaling in a cell in response to radiation therapy. Using gene expression profiles and radiation survival assays in an algorithm, a systems model was generated of the radiosensitivity network. The network consists of ten highly interconnected genetic hubs with significant signal redundancy. The model was validated with in vitro tests perturbing network components, correctly predicting radiation sensitivity ⅔ times. The model's clinical relevance was shown by linking clinical radiosensitivity targets to the model network. Clinical applications were confirmed by testing model predictions against clinical response to preoperative radiochemotherapy in patients with rectal or esophageal cancer.

12 Claims, 25 Drawing Sheets

(56) References Cited

OTHER PUBLICATIONS

Browman et al., "Choosing a concomitant chemotherapy and radiotherapy regimen for squamous cell head and neck cancer: A systematic review of the published literature with subgroup analysis," Head & Neck, 23:579-589 (2001).
Bucci et al., "Advances in Radiation Therapy: Conventional to 3D, to IMRT, to 4D, and Beyond," CA Cancer J Clin, 55:117-134 (2005).
Buffa et al., "Incorporating biologic measurements (SF(2), CFE) into a tumor control probability model increases their prognostic significance: a study in cervical carcinoma treated with radiation therapy," Int J Radiat Oncol Biol Phys, 50(5):1113-1122 (2001).
Capirci et al., "Prognostic Value of Pathologic Complete Response After Neoadjuvant Therapy in Locally Advanced Rectal Cancer: Long-term Analysis of 566 ypCR Patients," International Journal of Radiation Oncology Biology Physics, 72(1):99-107 (2008).
Cerna et al., "Histone deacetylation as a target for radiosensitization," Curr Top Dev Biol, 73:173-204 (2006).
Chang et al., "GATHER: a systems approach to interpreting genomic signatures," Bioinformatics, 22:2926-2933 (2006).
Chen et al., "Downstaging of advanced rectal cancer following combined preoperative chemotherapy and high dose radiation," International Journal of Radiation Oncology, Biology, Physics, 30:169-175 (1994).
Chinnaiyan et al., "Modulation of radiation response by histone deacetylase inhibition," Int J Radiat Oncol Biol Phys, 62:223-229 (2005).
Chirieac et al., "Post therapy pathologic stage predicts survival in patients with esophageal carcinoma receiving preoperative chemoradiation," Cancer, 103:1347-1355 (2005).
Cho et al., "Topoisomerase I inhibitors in the combined-modality therapy of lung cancer," Oncology, 18:29-39 (2004).
Chung et al., "Molecular classification of head and neck squamous cell carcinomas using patterns of gene expression," Cancer Cell, 5:489-500 (2004).
Corvo et al., "In vivo cell kinetics in head and neck squamous cell carcinomas predicts local control and helps guide radiotherapy regimen," J Clin Oncol, 13:1843-1850 (1995).
Cox et al., "The dark side of Ras: regulation of apoptosis," Oncogene, 22:8999-9006 (2003).
Cuddihy et al., "The p53 protein family and radiation sensitivity: Yes or no?" Cancer Metastasis Rev, 23:237-257 (2004).
D'Amico et al., "6-Month Androgen Suppression Plus Radiation Therapy vs Radiation Therapy Alone for Patients With Clinically Localized Prostate Cancer: A Randomized Controlled Trial," JAMA, 292:821-827 (2004).
Dalton et al., "Cancer biomarkers—an invitation to the table," Science 312:1165-1168 (2006).
Deng et al., "Caenorhabditis Elegans ABL-1 Antogonizes P53-Mediated Germline Apoptosis After Ionizing Irradiation," Nature Genetics, 36:906-912 (2004).
Denis et al., "Final Results of the 94-01 French Head and Neck Oncology and Radiotherapy Group Randomized Trial Comparing Radiotherapy Alone With Concomitant Radiochemotherapy in Advanced-Stage Oropharynx Carcinoma," J Clin Oncol, 22:69-76 (2004).
Deschavanne et al., "A review of human cell radiosensitivity in vitro," Int J Radiat Oncol Biol Phys, 34(1):251-266 (1996).
Dobbin et al., "Interlaboratory comparability study of cancer gene expression analysis using oligonucleotide microarrays," Clin Cancer Res, 11:565-572 (2005).
Eifel et al., "Pelvic Irradiation With Concurrent Chemotherapy Versus Pelvic and Para-Aortic Irradiation for High-Risk Cervical Cancer: An Update of Radiation Therapy Oncology Group Trial (RTOG) 90-01," J Clin Oncol, 22:872-880 (2004).
El-Deiry, W. S., "The role of p53 in chemosensitivity and radiosensitivity," Oncogene, 22, 7486-7495 (2003).
Eschrich et al., "Molecular staging for survival prediction of colorectal cancer patients," J Clin Oncol, 23:3526-3535 (2005).
Eschwege et al., "Predictive assays of radiation response in patients with head and neck squamous cell carcinoma: a review of the Institute Gustave Roussy experience," Int J Radiat Oncol Biol Phys, 39:849-853 (1997).
Fertil et al., "Inherent cellular radiosensitivity as a basic concept for human tumor radiotherapy," Int J Radiat Oncol Biol Phys, 7(5):621-629 (1981).
Fertil et al., "Intrinsic radiosensitivity of human cell lines is correlated with radioresponsiveness of human tumors: analysis of 101 published survival curves," International Journal of Radiation Oncology, Biology, Physics, 11:1699-1707 (1985).
Fiorica et al., "Preoperative chemoradiotherapy for oesophageal cancer: a systematic review and meta-analysis," Gut, 53(7):925-930 (2004).
Fryknäs et al., "STAT1 signaling is associated with acquired crossresistance to doxorubicin and radiation in myeloma cell lines," International Journal of Cancer, 120:189-195 (2007).
Furuse et al., "Phase III Study of Concurrent Versus Sequential Thoracic Radiotherapy in Combination With Mitomycin, Vindesine, and Cisplatin in Unresectable Stage III Non-Small-Cell Lung Cancer," J Clin Oncol, 17:2692-2699 (1999).
Fyles et al., "Tumor hypoxia has independent predictor impact only in patients with node-negative cervix cancer," J Clin Oncol, 20:680-687 (2002).
Gavioli et al., "Incidence and Clinical Impact of Sterilized Disease and Minimal Residual Disease After Preoperative Radiochemotherapy for Rectal Cancer," Dis Colon Rectum, 48:1851-1857 (2005).
Giles et al., "Optimizing outcomes for patients with advanced disease in chronic myelogenous leukemia," Semin Oncol, 35:S1-17; quiz S18-20 (2008).
Gudkov et al., "The Role of p53 in Determining Sensitivity to Radiotherapy," Nature Reviews Cancer, 3:117-129 (2003).
Hallahan et al., "Prolonged c-jun expression in irradiated ataxia telangiectasia fibroblasts," International Journal of Radiation Oncology, Biology, Physics, 36:355-360 (1996).
Hallahan et al., "Radiation signaling mediated by Jun activation following dissociation from a cell type-specific repressor," J Biol Chem, 268:4903-4907 (1993).
Hanks et al., "Phase III Trial of Long-Term Adjuvant Androgen Deprivation After Neoadjuvant Hormonal Cytoreduction and Radiotherapy in Locally Advanced Carcinoma of the Prostate: The Radiation Therapy Oncology Group Protocol 92-02," J Clin Oncol, 21:3972-3978 (2003).
Hennequin et al., "Chemotherapy with cisplatinum, carboplatin and 5FU-folinic acid, followed by concomitant chemo-radiotherapy in unresectable esophageal carcinomas," Bull Cancer, 88(2):203-207 (2001).
Hennequin et al., "Impact on survival of surgery after concomitant chemoradiotherapy for locally advanced cancers of the esophagus," International Journal of Radiation Oncology, Biology, Physics, 49:657-664 (2001).
Herskovic et al., "Combined chemotherapy and radiotherapy compared with radiotherapy alone in patients with cancer of the esophagus," N Engl J Med, 326:1593-1598 (1992).
Hieronymus et al., "Gene expression signature-based chemical genomic prediction identifies a novel class of HSP90 pathway modulators," Cancer Cell, 10:321-330 (2006).
Hood L., Heath J.R., Phelps M.E., Lin B. "Systems biology and new technologies enable predictive andpreventative medicine," Science. Oct. 22, 2004. 306. 5696. pp. 640-643.
Hood L., Perlmutter R.M., "The impact of systems approaches on biological problems in drug discovery," Nat Biotechnol. Oct. 22, 2004. 10. pp. 1215-1217.
Irizarry et al., "Summaries of Affymetrix GeneChip probe level data," Nucleic Acids Res, 31:e15 (2003).
Janjan et al., "Improved Overall Survival Among Responders to Preoperative Chemoradiation for Locally Advanced Rectal Cancer," Am J Clin Oncol, 24:107-112 (2001).
Janjan et al., "Tumor downstaging and sphincter preservation with preoperative chemoradiation in locally advanced rectal cancer: the M. D. Anderson Cancer Center experience," International Journal of Radiation Oncology,Biology,Physics, 44:1027-1038 (1999).

(56) References Cited

OTHER PUBLICATIONS

Jassem, J., "Combined chemotherapy and radiation in locally advanced nonsmall-cell lung cancer," The Lancet Oncology, 2:335-342 (2001).
Jeong et al., "Lethality and centrality in protein networks," Nature, 411:41-42 (2001).
Jeong et al., "The large-scale organization of metabolic networks," Nature, 407(6804):651-654 (2000).
Jeremic et al., "Hyperfractionated radiation therapy with or without concurrent low-dose daily carboplatin/etoposide for stage III non-small-cell lung cancer: a randomized study," J Clin Oncol, 14:1065-1070 (1996).
Jeremic et al., "Hyperfractionated Radiation Therapy With or Without Concurrent Low-Dose Daily Cisplatin in Locally Advanced Squamous Cell Carcinoma of the Head and Neck: A Prospective Randomized Trial," J Clin Oncol, 18:1458-1464 (2000).
Jeremic et al., "Randomized trial of hyperfractionated radiation therapy with or without concurrent chemotherapy for stage III non-small-cell lung cancer," J Clin Oncol, 13:452-458 (1995).
Kaminski et al., "Effect of sequencing of androgen deprivation and radiotherapy on prostate cancer growth," International Journal of Radiation Oncology, Biology, Physics, 57:24-28 (2003).
Kao et al., "p34$^{Cdc2}$kinase activity is excluded from the nucleus during the radiation-induced $G_2$ arrest in HeLa cells," J Biol Chem, 274:34779-34784 (1999).
Keys et al., "Cisplatin, Radiation, and Adjuvant Hysterectomy Compared with Radiation and Adjuvant Hysterectomy for Bulky Stage IB Cervical Carcinoma," N Engl J Med, 340:1154-1161 (1999).
Khan et al., "Classification and diagnostic prediction of cancers using gene expression profiling and artificial neural networks," Nature Medicine, 7(6):673-679 (2001).
Kim et al., "The influence of Ras pathway signaling on tumor radiosensitivity," Cancer and Metastasis Reviews, 23:227-236 (2004).
Kitano, "Computational systems biology," Nature. Nov. 14, 2002. 420. 6912. pp. 206-210.
Kitano, "Systems biology: a brief overview." Science. Mar. 1, 2002. 295. 5560. pp. 1662-1664.
Lamb et al., "The Connectivity Map: Using Gene-Expression Signatures to Connect Small Molecules, Genes, and Disease," Science, 313:1929-1935 (2006).
Landry et al., "Preoperative irradiation and fluorouracil chemotherapy for locally advanced rectosigmoid carcinoma: phase I-II study," Radiology, 188:423-426 (1993).
Lawton et al., "Androgen suppression plus radiation versus radiation alone for patients with stage D1/pathologic node-positive adenocarcinoma of the prostate: updated results based on national prospective randomized trial Radiation Therapy Oncology Group 85-31," J Clin Oncol, 23:800-807 (2005).
Li et al., "AKT-independent protection of prostate cancer cells from apoptosis mediated through complex formation between the androgen receptor and FKHR," Mol Cell Biol, 23:104-118 (2003).
Li et al., "Ionizing radiation and short wavelength UV activate NF-kappa B through two distinct mechanisms," PNAS, 95:13012-13017 (1998).
Lindsay et al., "The genetic basis of tissue responses to ionizing radiation," Br J Radiol, 80:S2-6 (2007).
Liu et al., "NF-[kappa]B Is Required for UV-Induced JNK Activation via Induction of PKCδ," Molecular Cell, 21:467-480 (2006).
Lorvidhaya et al., "Concurrent mitomycin C, 5-fluorouracil, and radiotherapy in the treatment of locally advanced carcinoma of the cervix: a randomized trial," International Journal of Radiation Oncology,Biology,Physics, 55:1226-1232 (2003).
Ma et al., "Combined-Modality Treatment of Solid Tumors Using Radiotherapy and Molecular Targeted Agents," J Clin Oncol, 21:2760-2776 (2003).
Malaise et al., "Distribution of radiation sensitivities for human tumor cells of specific histological types: comparison of in vitro to in vivo data," International Journal of Radiation Oncology, Biology, Physics, 12:617-624 (1986).

Mao et al., "SUMO-1 conjugation to topoisomerase I: A possible repair response to topoisomerase-mediated DNA damage," Proc Natl Acad Sci U S, A97:4046-4051 (2000).
Marples et al., "Low-dose hyper-radiosensitivity: past, present, and future," Int J Radiat Oncol Biol Phys, 70:1310-13188 (2008).
Massague, J., "Sorting out breast-cancer gene signatures," N. Engl. J. Med., 356: 294-297 (2007).
Mialon et al., "DNA topoisomerase I is a cofactor for c-Jun in the regulation of epidermal growth factor receptor expression and cancer cell proliferation," Mol. Cell Biol., 25:5040-5051 (2005).
Milas et al., "Chemoradiotherapy: Emerging treatment improvement strategies" Head & Neck, 25:152-167 (2003).
Minsky et al., "Enhancement of radiation-induced downstaging of rectal cancer by fluorouracil and high-dose leucovorin chemotherapy," J. Clin. Oncol., 10:79-84 (1992).
Moeller et al., "Hypoxia and radiotherapy: opportunities for improved outcomes in cancer treatment," Cancer Metastasis Rev., 26:241-248 (2007).
Mohiuddin et al., "Preoperative chemoradiation in fixed distal rectal cancer: dose time factors for pathological complete response," International Journal of Radiation Oncology, Biology, Physics, 46:883-888 (2000).
Mohiuddin et al., "Prognostic significance of postchemoradiation stage following preoperative chemotherapy and radiation for advanced/recurrent rectal cancers," Int. J. Radiat. Oncol. Biol. Phys., 48(4):1075-1080 (2000).
Morris et al., "Pelvic Radiation with Concurrent Chemotherapy Compared with Pelvic and Para-Aortic Radiation for High-Risk Cervical Cancer," N. Engl. J. Med., 340:1137-1143 (1999).
Movsas et al., "Hypoxic prostate/muscle pO2 ratio predicts for biochemical failure in patients with prostate cancer: preliminary findings," Urology, 60:634-639 (2002).
Nahta et al., "Mechanisms of disease: understanding resistance to HER2-targeted therapy in human breast cancer," Nat. Clin. Pract. Oncol., 3:269-280 (2006).
Nakajima et al., "Involvement of protein kinase C-related anti-apoptosis signaling in radiation-induced apoptosis in murine thymic lymphoma(3SBH5) cells," Radiat. Res., 161:528-534 (2004).
Nakajima et al., "Regulation of radiation-inducted protein kinase Cdelta activation in radiation-induced apoptosis differs between radiosensitive and radioresistant mouse thymic lymphoma cell lines," Mutat. Res., 595(1-2):29-36 (2006).
Narlikar et al., "Cooperation between Complexes that Regulate Chromatin Structure and Transcription," Cell, 108:475-487 (2002).
Office Action issued in U.S. Appl. No. 10/904,326 on Dec. 11, 2008.
Office Action issued in U.S. Appl. No. 10/904,326 on Dec. 12, 2007.
Office Action issued in U.S. Appl. No. 10/904,326 on May 22, 2007.
Office Action issued in U.S. Appl. No. 10/904,326 on May 29, 2008.
Pamment et al., "Regulation of the IRF-1 tumour modifier during the response to genotoxic stress involves an ATM-dependent signalling pathway," Oncogene, 21:7776-7785 (2002).
Peeters et al., "Acute and late complications after radiotherapy for prostate cancer: results of a multicenter randomized trial comparing 68 Gy to 78 Gy," Int. J. Radiat. Oncol. Biol. Phys., 61:1019-1034 (2005).
Perez, C., "Principles and Management of Radiation Therapy," Philadelphia-New York, Lippincott-Raven (1998).
Peters et al., "Concurrent Chemotherapy and Pelvic Radiation Therapy Compared With Pelvic Radiation Therapy Alone as Adjuvant Therapy After Radical Surgery in High-Risk Early-Stage Cancer of the Cervix," J. Clin. Oncol., 18:1606-1613 (2000).
Peters et al., "Predictive assays of tumor radiocurability," Am. J. Clin. Oncol., 11(3):275-287 (1988).
Peters, LJ, "The ESTRO Regaud lecture. Inherent radiosensitivity of tumor and normal tissue cells as a predictor of human tumor response," Radiother. Oncol., 17(3):177-190 (1990).
Pilepich et al., "Phase III radiation therapy oncology group (RTOG) trial 86-10 of androgen deprivation adjuvant to definitive radiotherapy in locally advanced carcinoma of the prostate," International Journal of Radiation Oncology, Biology, Physics, 50:1243-1252 (2001).
Potti et al., "Genomic signatures to guide the use of chemotherapeutics," Nat. Med., 12:1294-1300 (2006).

(56) References Cited

OTHER PUBLICATIONS

Pramana et al., "Gene expression profiling to predict outcome after chemoradiation in head and neck cancer," Int. J. Radiat. Oncol. Biol. Phys., 69:1544-1552 (2007).
Qiu et al., "Molecular prognostic factors in rectal cancer treated by radiation and surgery," Dis. Colon Rectum, 43(4):451-459 (2000).
Reboul, F., "Radiotherapy and chemotherapy in locally advanced non-small cell lung cancer: preclinical and early clinical data," Hematol. Oncol. Clin. North. Am., 18:41-53 (2004).
Rich et al., "Preoperative infusional chemoradiation therapy for stage T3 rectal cancer," International Journal of Radiation Oncology, Biology, Physics, 32:1025-1029 (1995).
Rose al., "Concurrent Cisplatin-Based Radiotherapy and Chemotherapy for Locally Advanced Cervical Cancer," N. Engl. J. Med., 340:1144-1153 (1999).
Rosen et al., "Biological Basis of Radiation Sensitivity. Part 2: Cellular and Molecular Determinants of Radiosensitivity," Oncology, 14:741-757 (2000).
Russell et al., "Gleevec-Mediated Inhibition of Rad51 Expression and Enhancement of Tumor Cell Radiosensitivity," Cancer Res., 63:7377-7383 (2003).
Sauer et al., "Preoperative versus postoperative chemoradiotherapy for rectal cancer," N. Engl. J. Med., 351(17):1731-1740 (2004).
Schaake-Koning et al., "Effects of concomitant cisplatin and radiotherapy on inoperable non-small-cell lung cancer," N. Engl. J. Med., 326:524-530 (1992).
Shedden et al., "Gene expression-based survival prediction in lung adenocarcinoma: a multi-site, blinded validation study," Nat. Med., 14:822-827 (2008).
Simon et al., "Pitfalls in the Use of DNA Microarray Data for Diagnostic and Prognostic Classification," J. Natl. Cancer. Inst., 95:14-18 (2003).
Staunton et al., "Chemosensitivity prediction by transcriptional profiling," Proc Natl Acad Sci U S A. Sep. 11, 2001. 98. 19. pp. 10787-10792.
Stausbol-Gron et al., "Relationship between tumour cell in vitro radiosensitivity and clinical outcome after curative radiotherapy for squamous cell carcinoma of the head and neck," Radiother. Oncol., 50(1):47-55 (1999).
Taghian et al., "Intrinsic radiation sensitivity may not be the major determinant of the poor clinical outcome of glioblastoma multiforme," Int. J. Radiat. Oncol. Biol. Phys., 25(2):243-249 (1993).
Tannapfel et al., "Apoptosis, proliferation, bax, bcl-2 and p53 status prior to and after preoperative radiochemotherapy for locally advanced rectal cancer," Int. J. Radiat. Oncol. Biol. Phys., 41(3):585-91(1998).
Tepper et al., "Superiority of trimodality therapy to surgery alone in esophageal cancer: Results of CALGB 9781," In: ASCO. San Francisco, (2006).
Terzoudi et al., "Increased G2 chromosomal radiosensitivity in cancer patients: the role of cdkl/cyclin-B activity level in the mechanisms involved," Int. J. Radiat. Biol., 76:607-615 (2000).
Torres-Roca et al., "Prediction of radiation sensitivity using a gene expression classifier," Cancer Res. Aug. 15, 2005. 65. 16. pp. 7169-7176.
Tusher et al., "Significance analysis of microarrays applied to the ionizing radiation response," Proc. Natl. Acad. Science USA, 98(9):5116-5121 (2001).
Van de Vijver et al., "A gene-expression signature as a predictor of survival in breast cancer," N. Engl. J. Med., 347:1999-2009 (2002).
Van Gelder et al., "Amplified RNA synthesized from limited quantities of heterogeneous cDNA," Proc. Natl. Acad. Sci. USA, 87:1663-1667 (1990).
Van 'T Veer et al., "Gene expression profiling predicts clinical outcome of breast cancer," Nature, 415:530-536 (2002).
Wang et al., "DNA repair factor XPC is modified by SUMO-1 and ubiquitin following UV irradiation," Nucleic Acids Res., 33:4023-4034 (2005).
Voy et al., "Extracting gene networks for low-dose radiation using graph theorectical algorithms," Computational Biology, vol. 2, Issue 7, pp. 0757-0768, Jul. 2006.
Wang et al., "Loss of Tumor Suppressor p53 Decreases PTEN Expression and Enhances Signaling Pathways Leading to Activation of Activator Protein 1 and Nuclear Factor {kappa} B Induced by UV Radiation," Cancer Res., 65:6601-6611 (2005).
Watanbe et al., "Prediction of sensitivity of rectal cancer cells in response to preoperative radiotherapy by DNA microarray analysis of gene expression profiles," Cancer Res., 66:3370-3374 (2006).
Wei et al., "Gene expression-based chemical genomics identifies rapamycin as a modulator of MCL1 and glucocorticoid resistance," Cancer Cell, 10:331-342 (2006).
Weichselbaum et al., "An interferon-related gene signature for DNA damage resistance is a predictive marker for chemotherapy and radiation for breast cancer," Proc. Natl. Acad. Sci. USA, 105(47):18490-18495 (2008).
Wendt et al., "Simultaneous radiochemotherapy versus radiotherapy alone in advanced head and neck cancer: a randomized multicenter study," J. Clin. Oncol., 16:1318-1324 (1998).
West et al., "Intrinsic radiosensitivity and prediction of patient response to radiotherapy for carcinoma of the cervix," Br. J. Cancer, 68:819-823 (1993).
West et al., "The independence of intrinsic radiosensitivity as a prognostic factor for patient response to radiotherapy of carcinoma of the cervix," British Journal of Cancer, 76:1184-1190 (1997).
Whitney et al., "Randomized Comparison of Fluorouracil Plus Cisplatin Versus Hydroxyurea as an Adjunct to Radiation Therapy in Stage IIB-IVA Carcinoma of the Cervix With Negative Para-Aortic Lymph Nodes: A Gynecologic Oncology Group and Southwest Oncology Group Study," J. Clin. Oncol., 17:1339-1348 (1999).
Wong et al., "Gene expression pattern associated with radiotherapy sensitivity in cervical cancer," Cancer J., 12:189-193 (2006).
Xu et al., "Merging microarray data from separate breast cancer studies provides a robust prognostic test," BMC Bioinformatics, 9:125 (2008).
Zelefsky et al., "High Dose Radiation Delivered by Intensity Modulated Conformal Radiotherapy Improves the Outcome of Localized Prostate Cancer," The Journal of Urology, 166:876-881 (2001).
Zhang et al., "FoxO1 regulates multiple metabolic pathways in the liver: effects on gluconeogenic, glycolytic, and lipogenic gene expression," J. Biol. Chem., 281(15):10105-10117 (2006).
Eschrich et al., "Towards Personalized Radiation Therapy: Translation of a Mathematical Model of Radiosensitivity Network to the Prediction of Clinical Radiation Response" International Journal of Radiation Oncology*Biology*Physics, vol. 69(3, Suppl): S595 (Abstract #2713, American Society for Radiation Oncology (ASTRO) 49th Annual Meeting, Oct. 2007.
Eschrich et al., "Mathematical Modeling of Radiation Response," Oasis, The Online Abstract Submission System, Abstract #3804: American Association for Cancer Research (AACR) 98th Annual Meeting, Los Angeles, CA, Apr. 2007, 3 pages.
Eschrich et al., "Mathematical Modeling of the Radiation Response Network," Poster, American Association for Cancer Research (AACR) 98th Annual Meeting, Apr. 2007, 1 page.
Eschrich et al., "Mathematical Modeling of the Radiation Response Network," Abstract #3804, American Association for Cancer Research (AACR) 98th Annual Meeting, Apr. 2007, 2 pages.
Eschrich et al., "Towards Personalized Radiation Therapy: Translation of a Mathematical Model of the Radiation Sensitivity Network to the Prediction of Clinical Radiation Response," Poster, American Society for Radiation Oncology (ASTRO) 49th Annual Meeting, Oct. 2007, 1 page.
Torres-Roca, "A Multi-Gene Expression Model to Predict Tumor Radiosensitivity," Talk, RTOG Semi Annual Meeting, GU TRP Committee, Philadelphia, PA, Jun. 2008, 15 pages.
Torres-Roca, "Mathematical Models, Molecular Signatures and the Prediction of Response to Radiation Therapy," Talk, National Functional Genomics Center (NFGC) 5th Annual External Advisory Board Meeting, Clearwater, FL, Oct. 2007, 32 pages.

(56) References Cited

OTHER PUBLICATIONS

Torres-Roca, "Predicting Clinical Response to Concurrent Radiochemotherapy Using a Systems Model of Radiosensitivity," Invited talk, City of Hope Medical Center, Duarte, CA), Jan. 2008, 32 pages.

Torres-Roca, "Prediction of Clinical Response to Concurrent Radiochemotherapy Using a Systems Model of Radiosensitivity," Talk, Radiation Therapy Oncology Group (RTOG) Semi Annual Meeting, Jan. 2008, 20 pages.

Torres-Roca; "Mathematical Models, Molecular Signatures and the Prediction of Response to Radiation Therapy," Talk, 1st Annual Total Cancer Care Summit, Paradise Island, Bahamas, Oct. 2007, 31 pages.

Pamment et al., "Regulation of the IRF-1 Tumour Modifier the Response to Genotoxic Stress Involves an ATM-Dependent Signalling Pathway," Oncogene, 21:7776-7785 (2002).

Zhang et al., "Biological Validation of a Linear Regression Mathematical Model of Gene Expression and Radiation Response," Poster, American Association for Cancer Research (AACR) 98th Annual Meeting, Los Angeles, CA, Apr. 2007, 1 page.

Zhang et al., "Biological Validation of a Linear Regression Mathematical Model of Gene Express and Radiation Response" (Short title "Mathematical Model of Radiation Response"), Abstract #3804, American Association for Cancer Research (AACR) 98th Annual Meeting, Los Angeles, CA, Apr. 2007, 3 pages.

Eschrich et al., "Systems Biology Modeling of the Radiation Sensitivity Network: A Biomarker Discovery Platform," *International Journal of Radiation: Oncology Biology Physics, Pergamon Press, USA*, vol. 75, No. 2, pp. 497-505, Oct. 1, 2009.

Extended European Search Report; Application No. 08831180.8-1408 / 2195005; mailed Mar. 11, 2013; Applicant: University of South Florida; 7 pages.

* cited by examiner

| Map | Map Folders | Cell process | p-Value | Genes Identified | Genes in Pathway |
|---|---|---|---|---|---|
| Role of AP-1 in regulation of cellular metabolism | Function groups/Transcription factors Regulation of metabolism | transcription | 8.322E-07 | 10 | 43 |
| Serotonin - melatonin biosynthesis and metabolism | Metabolic maps/Metabolism of mediators | | 0.0002761 | 5 | 19 |
| Alternative complement pathway | Cell signaling/Immune response | immune response | 0.000718 | 5 | 23 |
| Putative SUMO-1 pathway | Cell signaling/Proteolysis | proteolysis | 0.00216 | 5 | 29 |
| Role of VDR in regulation of genes involved in osteoporosis | Function groups/Transcription factors | transcription | 0.002307 | 7 | 57 |
| Androstenedione and testosterone biosynthesis and metabolism p.1 | Metabolic maps/Steroid metabolism | | 0.002841 | 4 | 19 |
| Ligand-Dependent Transcription of Retinoid-Target genes | Cell signaling/Regulation of transcription Function groups/Transcription factors | transcription, transcription | 0.003169 | 10 | 111 |
| Glycolysis and gluconeogenesis p. 2 | Metabolic maps/Carbohydrates metabolism | | 0.007541 | 3 | 13 |
| WNT signaling pathway. Part 1. Degradation of beta-catenin in the absence WNT signaling | Cell signaling/Growth and differentiation/Growth and differentiation (common pathways) Cell signaling/Proteolysis | proteolysis, response to extracellular stimulus | 0.01194 | 4 | 28 |
| Role of heterochromatin protein 1 (HP1) family in transcriptional silencing | Cell signaling/Regulation of transcription | transcription | 0.01211 | 5 | 43 |

Figure 8A

| Map | Map Folders | Cell process | p-Value | Genes Identified | Genes in Pathway |
|---|---|---|---|---|---|
| Transcription regulation of granulocyte development | Cell signaling/Growth and differentiation/Hematopoiesis | response to extracellular stimulus | 0.01331 | 5 | 44 |
| GTP-XTP metabolism | Metabolic maps/Nucleotide metabolism | | 0.01369 | 6 | 61 |
| Cortisone biosynthesis and metabolism | Metabolic maps/Steroid metabolism | | 0.01629 | 3 | 17 |
| Role ASK1 under oxidative stress | Cell signaling/Regulation of transcription Function groups/Kinases Function groups/Transcription factors | transcription, transcription, protein kinase cascade | 0.01895 | 4 | 32 |
| CTP/UTP metabolism | Metabolic maps/Nucleotide metabolism | | 0.02096 | 6 | 67 |
| Role of Akt in hypoxia induced HIF1 activation | Cell signaling/Proteolysis Function groups/Kinases Function groups/Transcription factors | proteolysis, transcription, protein kinase cascade | 0.0222 | 5 | 50 |
| Notch activating pathway for NF-kB | Cell signaling/Growth and differentiation/Growth and differentiation (common pathways) Cell signaling/Regulation of transcription Function groups/Transcription factors | transcription, transcription, response to extracellular stimulus | 0.02559 | 4 | 35 |
| Erk Interactions: Inhibition of Erk | Function groups/Kinases | protein kinase cascade | 0.02937 | 7 | 92 |
| Assembly of RNA Polymerase II preinitiation complex on TATA-less promoters | Cell signaling/Regulation of transcription | transcription | 0.03071 | 4 | 37 |

Figure 8B

| Map | Map Folders | Cell process | p-Value | Genes Identified | Genes in Pathway |
|---|---|---|---|---|---|
| ATP/ITP metabolism | Metabolic maps/Nucleotide metabolism | | 0.0323 | 6 | 74 |
| Estradiol metabolism | Metabolic maps/Steroid metabolism | | 0.03277 | 3 | 22 |
| Propionate metabolism p.2 | Metabolic maps/Carbohydrates metabolism | | 0.03277 | 3 | 22 |
| Lectin Induced complement pathway | Cell signaling/Immune response | immune response | 0.03638 | 4 | 39 |
| Bile Acid Biosynthesis | Metabolic maps/Steroid metabolism | | 0.03681 | 3 | 23 |
| Glucocorticoid receptor signaling | Cell signaling/Growth and differentiation/Growth and differentiation (common pathways) Cell signaling/Regulation of transcription Function groups/Hormones Function groups/Transcription factors | response to hormone stimulus, transcription, transcription, response to extracellular stimulus | 0.03942 | 4 | 40 |
| Leucine, isoleucine and valine metabolism.p.2 | Metabolic maps/Aminoacid metabolism | | 0.0456 | 3 | 25 |
| IL1 signaling pathway | Cell signaling/Immune response Function groups/Cyto/chemokines | cytokine and chemokine mediated signaling pathway, immune response | 0.04941 | 4 | 43 |
| WNT signaling pathway. Part 2 | Cell signaling/Growth and differentiation/Growth and differentiation (common pathways) | response to extracellular stimulus | 0.04942 | 6 | 82 |

Figure 8C

| Dynamic State | Map | Cell Process | p value |
|---|---|---|---|
| 2 | Role of Akt in hypoxia induced HIF1 activation | transcription, proteolysis, protein kinase cascade | 0.00059 |
| | Glycolysis and gluconeogenesis | Carbohydrates metabolism | 0.00066 |
| | Role of AP-1 in regulation of cellular metabolism | transcription | 0.02093 |
| 3 | Role SCF complex in cell cycle regulation | cell cycle | 0.00349 |
| | Role of AP-1 in regulation of cellular metabolism | transcription | 0.00428 |
| | Role APC in cell cycle regulation | cell cycle | 0.00769 |
| 4 | Role ASK1 under oxidative stress | transcription, transcription, protein kinase cascade | 0.00010 |
| | Role of Brca1 and Brca2 in DNA repair | cell cycle | 0.00033 |
| | Role of IAP-proteins in apoptosis | cell death, apoptosis | 0.00188 |
| | Role of AP-1 in regulation of cellular metabolism | transcription | 0.00364 |
| | Chemokines and adhesion | cell adhesion | 0.00435 |
| | Regulation of G1/S transition (part 2) | cell cycle | 0.01252 |
| | ATM/ATR regulation of G1/S checkpoint | cell cycle | 0.02392 |
| | FAS signaling cascades | cell death, apoptosis | 0.02701 |
| | IL2 activation and signaling pathway | immune response | 0.03031 |

Figure 9.

| Map | Map Folders | Cell process | p-Value | | Genes |
|---|---|---|---|---|---|
| Role of Akt in hypoxia induced HIF1 activation | Cell signaling/Proteolysis Function groups/Kinases Function groups/Transcription factors | proteolysis, transcription, protein kinase cascade | 0.00059 | 5 | 50 |
| Glycolysis and gluconeogenesis p. 2 | Metabolic maps/Carbohydrates metabolism | | 0.000655 | 3 | 13 |
| Role ASK1 under oxidative stress | Cell signaling/Regulation of transcription Function groups/Kinases Function groups/Transcription factors | transcription, transcription, protein kinase cascade | 0.00091 | 4 | 32 |
| * Role of IAP-proteins in apoptosis | Cell signaling/Cell death/Apoptosis | cell death, apoptosis | 0.001429 | 4 | 36 |
| Cortisone biosynthesis and metabolism | Metabolic maps/Steroid metabolism | | 0.001496 | 3 | 17 |
| Role of Parkin in the Ubiquitin-Proteasomal Pathway | Cell signaling/Proteolysis | proteolysis | 0.005542 | 4 | 52 |
| Parkin disorder under Parkinson's disease | Disease maps/Neurodisease/Parkinson's Disease | | 0.005542 | 4 | 52 |
| Putative ubiquitin pathway | Cell signaling/Proteolysis | proteolysis | 0.00859 | 3 | 31 |
| * Glycolysis and gluconeogenesis (short map) | Metabolic maps/Carbohydrates metabolism | | 0.01298 | 3 | 36 |
| Glucocorticoid receptor signaling | Cell signaling/Growth and differentiation/Growth and differentiation (common pathways) Cell signaling/Regulation of transcription Function groups/Hormones Function groups/Transcription factors | response to hormone stimulus, transcription, transcription, response to extracellular stimulus | 0.01726 | 3 | 40 |
| Role of AP-1 in regulation of cellular metabolism | Function groups/Transcription factors Regulation of metabolism | transcription | 0.02093 | 3 | 43 |

Figure 10A

| Map | Map Folders | Cell process | p-Value | | Genes |
|---|---|---|---|---|---|
| Role of heterochromatin protein 1 (HP1) family in transcriptional silencing | Cell signaling/Regulation of transcription | transcription | 0.02093 | 3 | 43 |
| Androstenedione and testosterone biosynthesis and metabolism p.3 | Metabolic maps/Steroid metabolism | | 0.0222 | 2 | 17 |
| * Cytoskeleton remodeling | Cell signaling/Cell adhesion | cell adhesion | 0.03433 | 6 | 176 |
| Bile Acid Biosynthesis | Metabolic maps/Steroid metabolism | | 0.03915 | 2 | 23 |
| * Ligand-dependent activation of the ESR1/AP-1 pathway | Function groups/Hormones Function groups/Transcription factors | response to hormone stimulus, transcription | 0.04233 | 2 | 24 |
| * Role of DAP12 receptors in NK cells | Cell signaling/Immune response | immune response | 0.04909 | 3 | 60 |

Figure 10B

| Map | Map Folders | Cell process | p-Value | Genes Identified | Genes in Pathway |
|---|---|---|---|---|---|
| * Ligand-dependent activation of the ESR1/SP pathway | Function groups/Hormones Function groups/Transcription factors | response to hormone stimulus, transcription | 0.003485 | 3 | 40 |
| * Role SCF complex in cell cycle regulation | Cell signaling/Cell cycle control | cell cycle | 0.003485 | 3 | 40 |
| Role of AP-1 in regulation of cellular metabolism | Function groups/Transcription factors Regulation of metabolism | transcription | 0.004282 | 3 | 43 |
| * Start of the mitosis | Cell signaling/Cell cycle control | cell cycle | 0.005838 | 3 | 48 |
| * Role APC in cell cycle regulation | Cell signaling/Cell cycle control | cell cycle | 0.007692 | 3 | 53 |
| * Oncostatin M signaling via JAK-Stat in mouse cells | Cell signaling/Immune response Function groups/Cyto/chemokines | cytokine and chemokine mediated signaling pathway, immune response | 0.008163 | 2 | 18 |
| Androstenedione and testosterone biosynthesis and metabolism p.1 | Metabolic maps/Steroid metabolism | | 0.009079 | 2 | 19 |
| * Oncostatin M signaling via JAK-Stat in human cells | Cell signaling/Immune response Function groups/Cyto/chemokines | cytokine and chemokine mediated signaling pathway, immune response | 0.009079 | 2 | 19 |
| * Prolactin receptor signaling | Function groups/Growth factors Function groups/Hormones | intracellular receptor-mediated signaling pathway, response to hormone stimulus | 0.01182 | 3 | 62 |
| * Regulation of G1/S transition (part1) | Cell signaling/Cell cycle control | cell cycle | 0.01182 | 3 | 62 |
| * Nucleocytoplasmic transport of CDK/Cyclins | Cell signaling/Cell cycle control | cell cycle | 0.01208 | 2 | 22 |
| * TPO signaling via JAK-STAT pathway | Cell signaling/Growth and differentiation/Hematopoiesis | response to extracellular stimulus | 0.01317 | 2 | 23 |

Figure 11A

| Map | Map Folders | Cell process | p-Value | Genes Identified | Genes in Pathway |
|---|---|---|---|---|---|
| Alternative complement pathway | Cell signaling/Immune response | immune response | 0.01317 | 2 | 23 |
| * Cell cycle (generic schema) | Cell signaling/Cell cycle control | cell cycle | 0.01667 | 2 | 26 |
| * Role 14-3-3 proteins in cell cycle regulation | Cell signaling/Cell cycle control | cell cycle | 0.01791 | 2 | 27 |
| * Brca1 as transcription regulator | Cell signaling/Cell cycle control Cell signaling/Regulation of transcription | cell cycle, transcription | 0.02187 | 2 | 30 |
| IFN alpha/beta signaling pathway | Cell signaling/Immune response Function groups/Cyto/chemokines | cytokine and chemokine mediated signaling pathway, immune response | 0.02187 | 2 | 30 |
| * Regulation of Apoptosis by Mitochondrial Proteins | Cell signaling/Cell death/Apoptosis | cell death, apoptosis | 0.02469 | 2 | 32 |
| * Chromosome condensation in prometaphase | Cell signaling/Cell cycle control | cell cycle | 0.02616 | 2 | 33 |
| * p53-dependent apoptosis | Cell signaling/Cell death/Apoptosis Function groups/Transcription factors | transcription, cell death, apoptosis | 0.02616 | 2 | 33 |
| * Sister chromatid cohesion | Cell signaling/Cell cycle control | cell cycle | 0.02919 | 2 | 35 |
| Vitamin K metabolism | Metabolic maps/Vitamin and cofactor metabolism | | 0.0302 | 1 | 4 |
| * CNTF receptor signaling | Function groups/Cyto/chemokines | cytokine and chemokine mediated signaling pathway | 0.03235 | 2 | 37 |
| * Transcription factor Tubby signaling pathways | Cell signaling/Regulation of transcription Function groups/G-proteins/GPCR Function groups/Transcription factors | transcription, transcription, G-protein coupled receptor protein signaling pathway | 0.04081 | 2 | 42 |

Figure 11B

| Map | Map Folders | process | p-value | Genes Identified | Genes in Pathway |
|---|---|---|---|---|---|
| * Oncostatin M signaling via MAPK in mouse cells | Cell signaling/Immune response Function groups/Cyto/chemokines | cytokine and chemokine mediated signaling pathway, immune response | 0.04081 | 2 | 42 |
| IL1 signaling pathway | Cell signaling/Immune response Function groups/Cyto/chemokines | cytokine and chemokine mediated signaling pathway, immune response | 0.0426 | 2 | 43 |
| Role of heterochromatin protein 1 (HP1) family in transcriptional silencing | Cell signaling/Regulation of transcription | transcription | 0.0426 | 2 | 43 |
| * Start of DNA replication in early S phase | Cell signaling/Cell cycle control | cell cycle | 0.0426 | 2 | 43 |
| * Oncostatin M signaling via MAPK in human cells | Cell signaling/Immune response Function groups/Cyto/chemokines | cytokine and chemokine mediated signaling pathway, immune response | 0.0426 | 2 | 43 |

Figure 11C

| Map | Map Folders | Cell process | p-Value | Genes Identified | Genes in Pathway |
|---|---|---|---|---|---|
| Formation of Sin3A and NuRD complexes and their role in transcription regulation | Cell signaling/Regulation of transcription | transcription | 5.28E-14 | 13 | 45 |
| Glucocorticoid receptor signaling | Cell signaling/Growth and differentiation/Growth and differentiation (common pathways), Cell signaling/Regulation of transcription, Function groups/Hormones Function groups/Transcription factors | response to hormone stimulus, transcription, transcription, response to extracellular stimulus | 2.44E-05 | 6 | 40 |
| Putative SUMO-1 pathway | Cell signaling/Proteolysis | proteolysis | 5.97E-05 | 5 | 29 |
| Role ASK1 under oxidative stress | Cell signaling/Regulation of transcription Function groups/Kinases Function groups/Transcription factors | transcription, transcription, protein kinase cascade | 9.76E-05 | 5 | 32 |
| Serotonin - melatonin biosynthesis and metabolism | Metabolic maps/Metabolism of mediators | | 0.000151 | 4 | 19 |
| Role of Brca1 and Brca2 in DNA repair | Cell signaling/Cell cycle control | cell cycle | 0.000326 | 5 | 41 |
| Role of VDR in regulation of genes involved in osteoporosis | Function groups/Transcription factors | transcription | 0.001506 | 5 | 57 |
| Antiviral actions of Interferons | Cell signaling/Immune response | immune response | 0.001545 | 3 | 16 |
| Role of IAP-proteins in apoptosis | Cell signaling/Cell death/Apoptosis | cell death, apoptosis | 0.001883 | 4 | 36 |
| Role of AP-1 in regulation of cellular metabolism | Function groups/Transcription factors Regulation of metabolism | transcription | 0.00364 | 4 | 43 |
| Chemokines and adhesion | Cell signaling/Cell adhesion Function groups/Cyto/chemokines | cytokine and chemokine mediated signaling pathway, cell adhesion | 0.004346 | 8 | 174 |
| Keratin filaments | Cell signaling/Cell adhesion | cell adhesion | 0.005421 | 4 | 48 |
| Parkin disorder under Parkinson's disease | Disease maps/Neurodisease/Parkinson's Disease | | 0.007205 | 4 | 52 |
| Role of Parkin in the Ubiquitin-Proteasomal Pathway | Cell signaling/Proteolysis | proteolysis | 0.007205 | 4 | 52 |
| Putative ubiquitin pathway | Cell signaling/Proteolysis | proteolysis | 0.01054 | 3 | 31 |
| Regulation of G1/S transition (part 2) | Cell signaling/Cell cycle control | cell cycle | 0.01252 | 3 | 33 |
| Assembly of RNA | | | | | |

Figure 12A

| Map | Map Folders | Cell process | p-Value | Genes Identified | Genes in Pathway |
|---|---|---|---|---|---|
| Polymerase II preinitiation complex on TATA-less promoters | Cell signaling/Regulation of transcription | transcription | 0.01708 | 3 | 37 |
| Angiotensin signaling via PYK2 | Cell signaling/Growth and differentiation/Angiopoiesis Function groups/G-proteins/GPCR | G-protein coupled receptor protein signaling pathway, response to extracellular stimulus | 0.02386 | 4 | 74 |
| ATM/ATR regulation of G1/S checkpoint | Cell signaling/Cell cycle control | cell cycle | 0.02392 | 3 | 42 |
| FAS signaling cascades | Cell signaling/Cell death/Apoptosis | cell death, apoptosis | 0.02701 | 3 | 44 |
| VEGF signaling via VEGFR2 - generic cascades | Cell signaling/Growth and differentiation/Angiopoiesis Function groups/Growth factors | intracellular receptor-mediated signaling pathway, response to extracellular stimulus | 0.02701 | 3 | 44 |
| Transcription regulation of granulocyte development | Cell signaling/Growth and differentiation/Hematopoiesis | response to extracellular stimulus | 0.02701 | 3 | 44 |
| cAMP signaling | Function groups/G-proteins/GPCR Function groups/Second messenger | second-messenger-mediated signaling, G-protein coupled receptor protein signaling pathway | 0.02789 | 5 | 115 |
| PDGF activation of prostacyclin synthesis | Cell signaling/Growth and differentiation/Growth and differentiation (common pathways) Function groups/Growth factors | intracellular receptor-mediated signaling pathway, response to extracellular stimulus | 0.02846 | 2 | 18 |
| IL2 activation and signaling pathway | Cell signaling/Immune response Function groups/Cyto/chemokines | cytokine and chemokine mediated signaling pathway, immune response | 0.03031 | 3 | 46 |
|  | Cell signaling/Regulation of transcription Function | transcription, |  |  |  |

Figure 12B

| Map | Map Folders | Cell process | p-Value | Genes Identified | Genes in Pathways |
|---|---|---|---|---|---|
| P53 signaling pathway | Cell signaling/Regulation of transcription Function groups/Transcription factors | transcription, transcription | 0.03031 | 3 | 46 |
| Start of the mitosis | Cell signaling/Cell cycle control | cell cycle | 0.03381 | 3 | 48 |
| Role of Akt in hypoxia induced HIF1 activation | Cell signaling/Proteolysis Function groups/Kinases Function groups/Transcription factors | proteolysis, transcription, protein kinase cascade | 0.03751 | 3 | 50 |
| Regulation of lipid metabolism by niacin and isoprenaline | Regulation of metabolism/Regulation of lipid metabolism | | 0.03943 | 3 | 51 |
| Propionate metabolism p.2 | Metabolic maps/Carbohydrates metabolism | | 0.04134 | 2 | 22 |
| Estradiol metabolism | Metabolic maps/Steroid metabolism | | 0.04134 | 2 | 22 |
| Angiotensin signaling via STATs | Cell signaling/Growth and differentiation/Angiopoiesis Function groups/G-proteins/GPCR | G-protein coupled receptor protein signaling pathway, response to extracellular stimulus | 0.04343 | 3 | 53 |
| Alternative complement pathway | Cell signaling/Immune response | immune response | 0.04485 | 2 | 23 |
| MIF-JAB1 signalling | Cell signaling/Immune response | immune response | 0.04485 | 2 | 23 |
| MIF in innate immunity response | Cell signaling/Immune response | immune response | 0.04978 | 3 | 56 |

Figure 12C

| Gene Set | Total Number of Probesets | Probesets Recognized in MetaCore |
|---|---|---|
| Top Genes | 500 | 485 |
| Dynamic State 2 | 187 | 184 |
| Dynamic State 3 | 115 | 112 |
| Dynamic State 4 | 198 | 193 |

Figure 14.

| Gene Name | Number of Edges | Number of Hidden Edges | HU6800 Probeset | U95Av2 Probeset | U133Plus Probeset |
|---|---|---|---|---|---|
| Androgen receptor | 19 | 0 | M23263_at | 1577_at | 211110_s_at |
| c-Jun | 19 | 4 | J04111_at | 1895_at | 201466_s_at |
| STAT1 | 15 | 1 | AFFX-HUMISGF3A/M97935_MA_at | AFFX-HUMISGF3A/M97935_MA_at | AFFX-HUMISGF3A/M97935_MA_at |
| PKC | 14 | 4 | X06318_at | 1217_g_at, 1336_s_at, 160029_at, 37301_at | 207957_s_at |
| RelA (p65) | 14 | 2 | U33838_at | 1045_s_at, 1295_at, 1271_g_at | 201783_s_at |
| c-Abl | 13 | 0 | X16416_at | 39730_at, 1636_g_at | 202123_s_at |
| SUMO-1 | 13 | 0 | U83117_at | 155_s_at, 157_s_at | 208762_at |
| PAK2 | 11 | 3 | U24153_at | 1559_at | 205962_at |
| HDAC | 10 | 0 | D50405_at | 38771_at | 201209_at |
| Integrin | 7 | 4 | | | |
| IRF1 | 7 | 0 | L05072_s_at | 669_s_at | 202531_at |
| PKC-beta | 6 | 5 | | | |
| Caspase-8 | 5 | 0 | | | |
| CDC25C | 5 | 4 | | | |
| Cyclin D1 | 5 | 0 | | | |
| FasR (CD95) | 5 | 0 | | | |
| Galpha(q)-specific peptide GPCRs | 5 | 5 | | | |
| HES1 | 5 | 0 | | | |

Figure 15.

| Tissue Type | R-Value | Prediction of c-jun knockdown |
|---|---|---|
| Lung Cancer | -0.69 | Radiation Resistance |
| Colon Cancer | 0.47 | No change or unequivocal |
| Breast Cancer | 0.94 | Radiosensitization |

Figure 16.

| Tissue of Origin | Cell Lines | n | SF2 (Mean ±S.D.), siRNA pool v. c-jun siRNA | p value |
|---|---|---|---|---|
| Lung | A549 | 5 | 0.52±0.13, 0.71±0.11 | 0.043 |
| | H460 | 9 | 0.50±0.06, 0.60±0.08 | 0.0072 |
| | Hop62 | 8 | 0.41±0.16, 0.50±0.18 | 0.267 |
| | Total | 22 | 0.47±0.11, 0.59±0.18 | 0.005 |
| Colon | HCT116 | 7 | 0.23±0.05, 0.30±0.06 | 0.052 |
| | HCT15 | 7 | 0.59±0.09, 0.66±0.13 | 0.251 |
| | HT29 | 5 | 0.85±0.21, 0.96±0.31 | 0.534 |
| | Total | 19 | 0.52±0.28, 0.60±0.32 | 0.41 |
| Breast | HS578 | 10 | 0.62±0.09, 0.67±0.07 | 0.709 |
| | MDA231 | 6 | 0.61±0.09, 0.67±0.11 | 0.335 |
| | Total | 16 | 0.62±0.09, 0.60±0.21 | |
| Overall | Total | 57 | 0.53±0.19, 0.60±0.21 | |

Figure 17.

| Cell Line | Predictions | Actual SF2 |
|---|---|---|
| BREAST_HS578T | 0.79 | 0.79 |
| BREAST_MDAMB231 | 0.16 | 0.82 |
| COLON_HCT116 | 0.47 | 0.38 |
| COLON_HCT15 | 0.55 | 0.4 |
| COLON_SW620 | 0.55 | 0.62 |
| LEUK_CCRFCEM | 0.48 | 0.185 |
| LEUK_HL60 | 0.52 | 0.315 |
| LEUK_MOLT4 | 0.4 | 0.05 |
| MELAN_SKMEL2 | 0.54 | 0.66 |
| NSCLC_A549ATCC | 0.53 | 0.61 |
| NSCLC_H460 | 0.65 | 0.84 |
| NSCLC_HOP62 | 0.31 | 0.164 |
| NSCLC_NCIH23 | 0.42 | 0.086 |
| OVAR_OVCAR5 | 0.61 | 0.408 |
| RENAL_SN12C | 0.41 | 0.62 |
| BREAST_BT549 | 0.72 | 0.632 |
| BREAST_MCF7 | 0.51 | 0.576 |
| BREAST_MDAMB435 | 0.52 | 0.1795 |
| BREAST_T47D | 0.45 | 0.52 |
| CNS_SF268 | 0.73 | 0.45 |
| CNS_SF539 | 0.62 | 0.82 |
| CNS_SNB19 | 0.59 | 0.43 |
| CNS_SNB75 | 0.74 | 0.55 |
| CNS_U251 | 0.82 | 0.57 |
| COLON_COLO205 | 0.57 | 0.69 |
| COLON_HCC-2998 | 0.54 | 0.44 |
| COLON_HT29 | 0.5 | 0.79 |
| COLON_KM12 | 0.4 | 0.42 |
| MELAN_LOXIMVI | 0.6 | 0.68 |
| MELAN_M14 | 0.46 | 0.42 |
| MELAN_MALME3M | 0.65 | 0.8 |
| MELAN_SKMEL28 | 0.53 | 0.74 |
| MELAN_SKMEL5 | 0.36 | 0.72 |
| MELAN_UACC257 | 0.52 | 0.48 |
| MELAN_UACC62 | 0.79 | 0.52 |
| NSCLC_EKVX | 0.43 | 0.7 |
| NSCLC_HOP92 | 0.36 | 0.43 |
| OVAR_OVCAR3 | 0.48 | 0.55 |
| OVAR_OVCAR4 | 0.34 | 0.29 |
| OVAR_OVCAR8 | 0.33 | 0.6 |
| OVAR_SKOV3 | 0.55 | 0.9 |
| PROSTATE_DU145 | 0.53 | 0.52 |
| PROSTATE_PC3 | 0.46 | 0.484 |
| RENAL_7860 | 0.54 | 0.66 |
| RENAL_A498 | 0.69 | 0.61 |
| RENAL_ACHN | 0.69 | 0.72 |
| RENAL_CAKI1 | 0.57 | 0.37 |
| RENAL_UO31 | 0.79 | 0.62 |

| SampleID | SF2 | Response |
|---|---|---|
| T4786A1 | 0.40 | R |
| T4839A1 | 0.32 | R |
| T4967A1 | 0.28 | R |
| T5344A1 | 0.33 | R |
| T5611A1 | 0.26 | R |
| T5649A1 | 0.32 | R |
| T5760A1 | 0.39 | R |
| T5903A1 | 0.27 | R |
| T5076A1 | 0.21 | NR |
| T5135A1 | 0.54 | NR |
| T5240A1 | 0.57 | NR |
| T5452A1 | 0.50 | NR |
| T5944A1 | 0.40 | NR |
| T6101A1 | 0.56 | NR |

B

| Target | Incoming | Outgoing |
|---|---|---|
| Topo-1 | c-Abl, PKC, SUMO-1 | c-jun |
| Ras/Raf/Mek/Erk | AR, PAK2, Stat1 | c-jun, AR |
| EGFR | AR, PKC | c-Abl, Stat1 |
| Cox-2 | c-jun, Stat1, NF-KB | |
| DNA-PK | c-Abl | c-Abl |
| Parp-1 | HDAC | NF-KappaB |
| Survivin | PAK2, NF-KB | |
| Hsp-90 | Stat1 | AR |
| TGF-Beta 1/2 | c-Jun, AR, NF-KB/HDAC1 | |

Figure 24.

PREDICTIVE RADIOSENSITIVITY NETWORK MODEL

CROSS REFERENCE TO RELATED APPLICATIONS

This application is a continuation of U.S. patent application Ser. No. 12/053,796, filed Mar. 24, 2008 now abandoned, which claims priority to U.S. Provisional Patent Application 60/896,350, entitled, "Radiation Response System Model", filed Mar. 22, 2007, and U.S. Provisional Patent Application 60/896,550, entitled, "Radiation Response System Model", filed Mar. 23, 2007 the contents of which are herein incorporated by reference.

STATEMENT OF GOVERNMENT INTEREST

This invention was made with Government support under Grant No. K08 CA 108926 awarded by the National Cancer Institute. The Government has certain rights in the invention.

FIELD OF INVENTION

This invention relates to cancer treatment. Specifically this invention is a predictive model of cancer radiosensitization.

BACKGROUND AND SUMMARY OF THE INVENTION

Understanding the biological networks that regulate oncogenic events and influence the inherent radiosensitivity of tumors is central to the development of personalized treatment strategies in radiation oncology, including targeted and improved therapeutic interventions. During the last two decades, many key components and signaling pathways in the oncogenic network have been elucidated by studying radiophenotypic changes after network components are perturbed. However, the dynamics of network component interactions have remained mostly undefined, largely due to lack of accurate testing methods.

The generation of high-throughput datasets in the "omic" era has been central to the development of a systems-view of complex biological systems. In systems biology, the goal is to understand the dynamics of the system and how components interact during operation (H. Kitano, Computational Systems Biology, Nature 420:6912, 2002, 206-210) (H. Kitano, Systems Biology: A Brief Overview, Science 295:5560, 2002, 1662-1664) (L. Hood, J. Heath, Systems Biology and New Technologies Enable Predictive and Preventative Medicine, Science, 306:5696, 2004, 640-643) (L. Hood, R. Perlmutter, The Impact of Systems Approaches on Biological Problems in Drug Discovery, Nat. Biotech., 22:10, 2004, 1215-1217). To study complex biological interactions within a network model, novel methods are needed. A central experimental approach in molecular biology has focused on studying biological systems after components are perturbed by activation/inactivation. A problem of this approach is that it is unable to capture and study the continuous nature of many phenotypic features in diseased and normal states. An alternative approach is a systems-view of biological networks where the focus is on understanding the dynamics and structure of the system of interest. A common feature of systems biology is the development of dry computational models which exploit comprehensive datasets of high-throughput measurements. A common denominator in these models is that biological hypothesis can be generated for testing in "wet" experiments, thus allowing the validation of the models and the dynamics studied. Computational models have been key in the development of central concepts in neurobiology.

SUMMARY OF THE INVENTION

Provided is a mathematical model that facilitates the study of radiation response by providing a systems view of the radiosensitivity network. The model predictions were tested against several biological and clinical endpoints. The systems-based approach improves the ability to define network dynamics and structure, allows the visualization of network topology, and provides a framework to understand its operation, thus leading to a better understanding of the variables that drive radiation sensitivity. Furthermore, as the model accounts for network interactions, the model to captures the variability of radiation response across biological/clinical conditions. This allows the possibility of developing an accurate predictive model of clinical radiosensitivity, a major clinical goal in radiation oncology.

A multivariate linear regression model of gene expression and radiosensitivity (SF2) was developed in a 48 cell line dataset within the context of an accurate radiation sensitivity classifier. A literature review of 35 cell lines in the dataset identified the radiation sensitivity of the cells using SF2 data. Radiation sensitivity for the remaining cell lines was established by establishing the genomic expression of each cell line. After a baseline gene expression dataset was obtained, the cells were irradiated with 2Gy and difference in gene expression determined using microarrays, which allowed for selection of expressed genes based on the gene's statistical correlation between the expression of the gene of interest and the radiation sensitivity of the cell line expressing the gene The genetic information for the cell line dataset was analyzed using the developed regression model, thereby identifying at least one gene of interest, which is predictive of a radiation response. The regression model identified 500 genes reactive to radiation induction. The 500 genes were analyzed using GeneGo to map interconnections between the genes, and identified a network of interacting genes. This data was further restricted by selecting genes with at least 5 connections to other genes and no more than 50% of the edges hidden within the network.

A series of dynamic cellular states were defined by incorporating biological interactions that has been shown to perturb radiosensitivity. The biological interactions of these common radiation response elements were defined by gene models using the best linear fit model and analyzing the variability of radiation response in multiple cell lines to identify the significant response elements.

The model was then applied to each gene in an expanded genomic/SF2 database of 48 cell lines. This design of an in silico model includes a diverse group of cancer cell lines and favors the identification of genes that are important across cell lines and are more likely central components of the radiation signaling network. The mathematical model also allows the development of biological predictions that can be confirmed by in vitro experiments. This allows feedback into whether the interpretations of the mathematics represented in the model are of biological value. Although the presence of multiple cell lines accounted for component variability, we sought to integrate actual dynamic states of the network. The hypothetical dynamic states were defined by incorporating into the linear regression model biological variables that have been reported to perturb the radiation response network: TO, ras status (mut/wt) and p53 status along with gene expression.

The resulting predictive algorithm identified five components of functional/biological relevance to the network that proved best at building the most accurate predictor, genes rbap48, top1, rgs19, r5pia and an unknown gene. rbap48 and rgs-19 were biologically-validated as network components. siRNA knockdown of rbap48 resulted in radioresistance in HCT-116 cell lines, while overexpression of rgs-19 led to radiosensitization of MDA-MB231 cell lines, both observations were consistent with model predictions. In contrast, overexpression of r5pia resulted in no radiophenotypic change of MALME-3M melanoma cells. Finally, top-1 is a clinically validated radiosensitizing target in current clinical use. Thus, we conclude that the linear regression model is reasonably accurate at identifying radiosensitivity network components.

The invention allows for predicting a clinical response to radiation therapy of a patient. Samples of the target cells were collected from the patients. The genomic expression of the collected sample was determined by microarray analysis and the data applied to the network model. High expression values correlated with a radiosensitive phenotype and predicted the clinical response to treatment with radiation therapy. In a specific embodiment, the target cells comprise cancerous cells.

A mathematical model has been developed to represent the topology of the radiation response network. The model identifies novel components of the radiation network as well as integrates dynamics and variability into biological predictions. Both of these abilities have been biologically validated. The model is also envisioned useful in biomarker discovery, allowing biomarkers of response or of radiophenotype to be identified using the model. The model is also useful for clinical trial designs. Network architecture proposed by the model has resulted in identified nodes, which allow for drug designs to specifically target those nodes. This is also useful to guide clinicians in proposing novel combinations of known drugs in clinical trials. Additionally the model may provide an approach to dissect the complexity of network operation. For example, a model detailing the contribution of each hub in the network to final system output can be derived from our database. Finally, a similar model is useful in identifying chemotherapy response using cellular/genomic databases.

BRIEF DESCRIPTION OF THE DRAWINGS

For a fuller understanding of the invention, reference should be made to the following detailed description, taken in connection with the accompanying drawings, in which:

FIGS. 8A-C are a table of the significant pathways defined by GeneGO MetaCore analysis for the top 500 genes identified by linear fit.

FIG. 9 is a table of selected pathways from the GeneGO MetaCore analysis of significant terms using ANOVA.

FIGS. 10A-B are a table of significant pathways found in Dynamic State 2.

FIGS. 11A-C are a table of significant pathways found in Dynamic State 3.

FIGS. 12A-C are a table of significant pathways found in Dynamic State 4.

FIG. 14 is a table showing the gene distribution of the data probeset against the dynamic states.

FIG. 15 is a table showing the radiation network hub genes. Genes in gray were used as central hubs for the classifier. The probesets used on each platform are listed for each hub.

FIG. 16 is a table showing the network model predictions for three cancer types.

FIG. 17 is a table of experimental data for three cancer types. The data validates the model predictions, seen in FIG. 16.

FIG. 19 is a table showing leave-one-out cross-validation predictions on the dataset cell lines using a rank-based linear classifier on the proposed radiation network hubs.

FIG. 24 is a table showing the manner in which radiosensitization targets are linked to the radiation sensitivity network.

DETAILED DESCRIPTION OF THE PREFERRED EMBODIMENT

Figure 1:
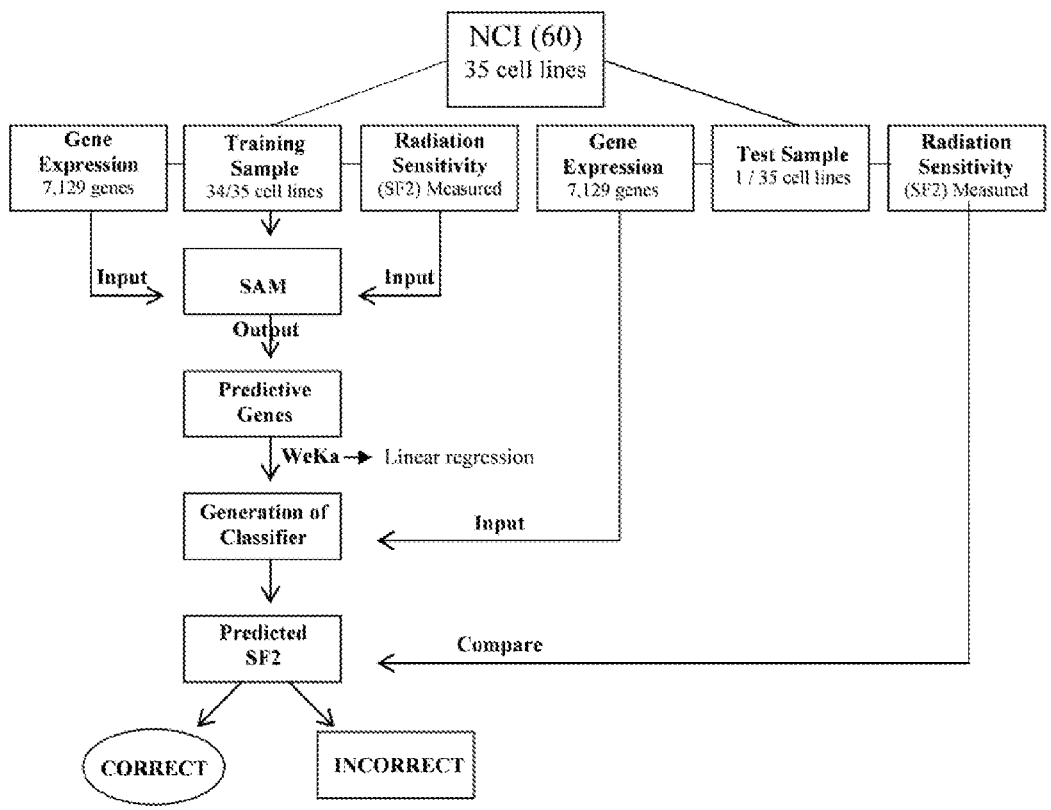
FIG. 1 is an illustration showing a flowchart of the multivariate linear regression model classifier algorithm.
Figure 2:
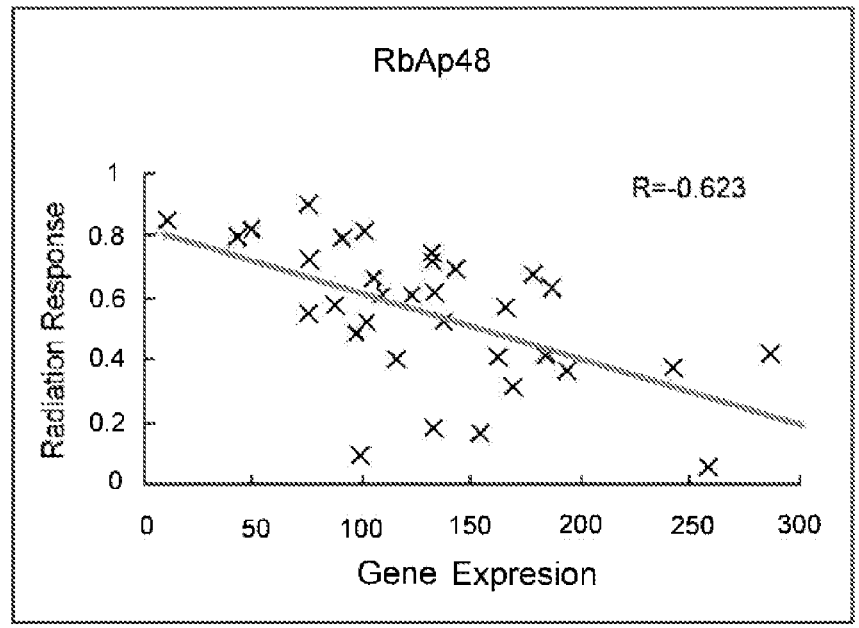
FIG. 2 is a graph showing the radiation response illustration showing the linear regression model output using RbAp48. The output predicts knockout of RbAp48 will result in radioresistance.
Figure 3:
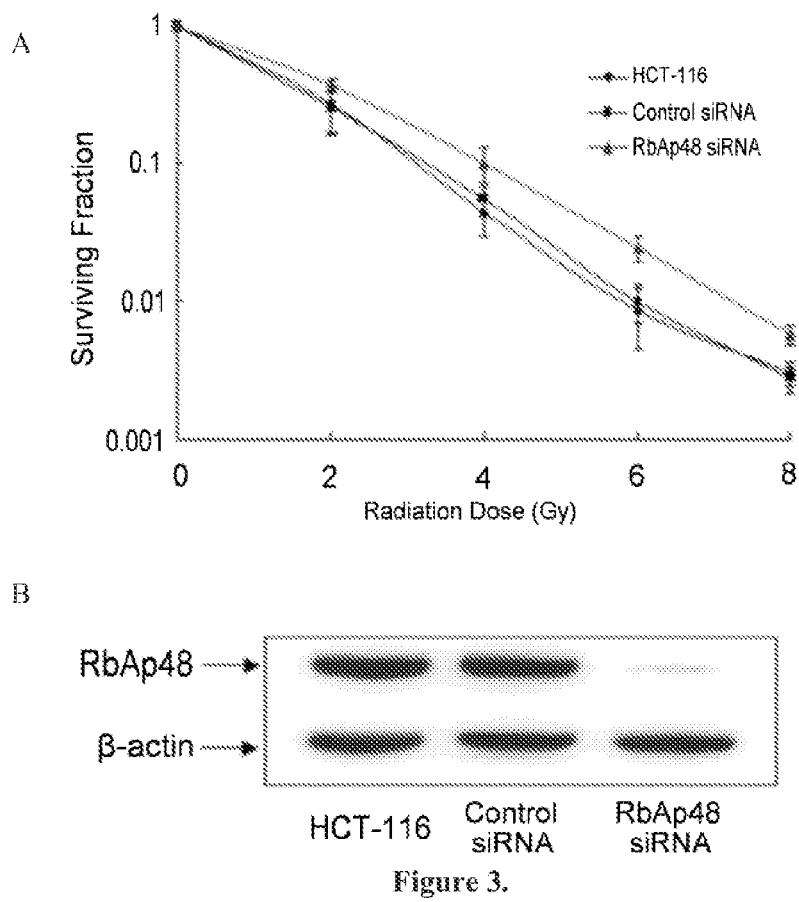
FIG. 3 shows the experimental outcome of knocking out RbAp48 in HCT116 cells. (A) Cell survival rates are graphed based on radiation exposure, and (B) a western blot of RbAp48 protein after siRNA transfection.
Figure 4:
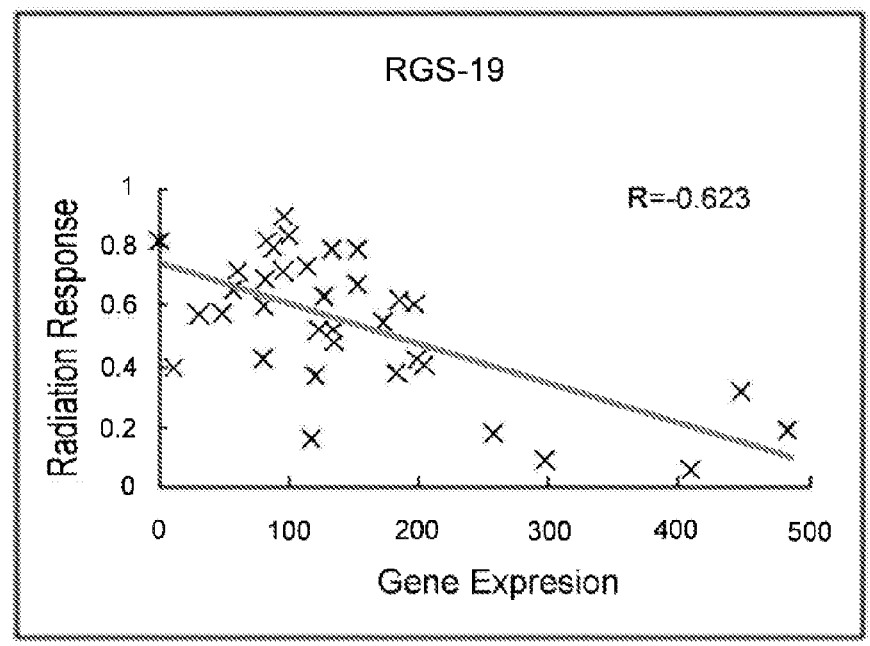
FIG. 4 is a graph showing the radiation response illustration showing the linear regression model output using RGS-19. The output predicts knockout of RGS-19 will result in radiosensitivity.
Figure 5:
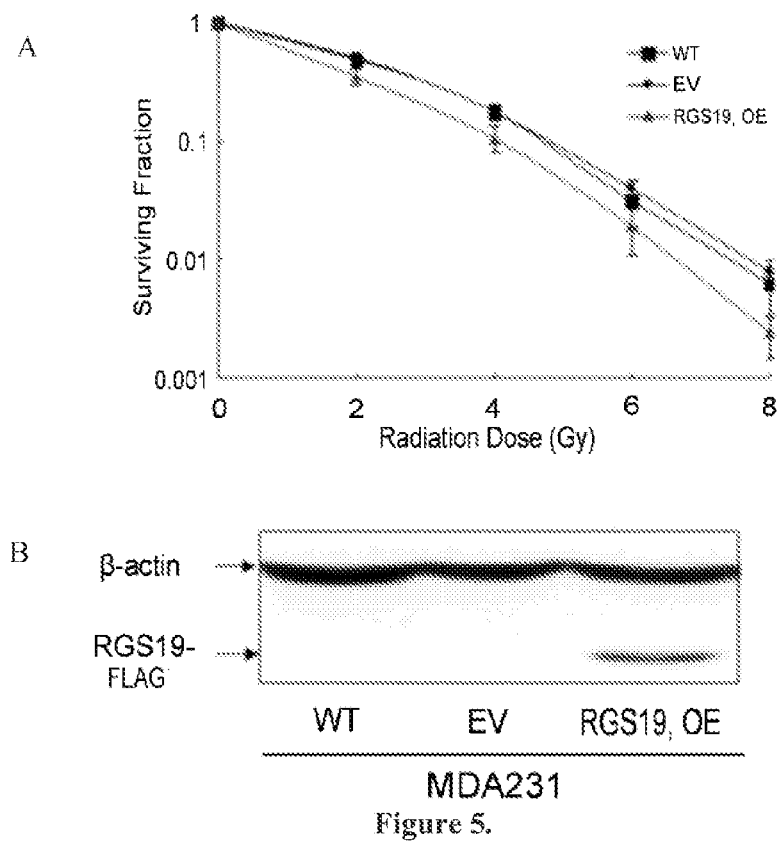
FIG. 5 shows the experimental outcome of knocking out RGS-19 in MDA231 cells. (A) Cell survival rates are graphed based on radiation exposure, and (B) a western blot of RGS-19 protein after siRNA transfection.
Figure 6:
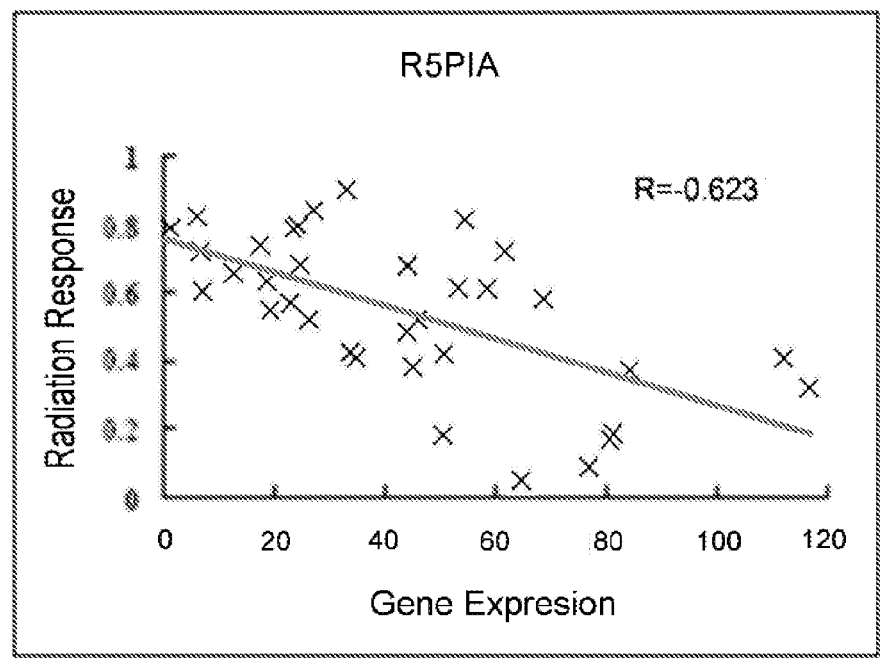
FIG. 6 is a graph showing the radiation response illustration showing the linear regression model output using Ribose 5 Phosphate Isomerase A (R5PIA). The output predicts overexpression of R5PIA will result in radiosensitivity.
Figure 7:
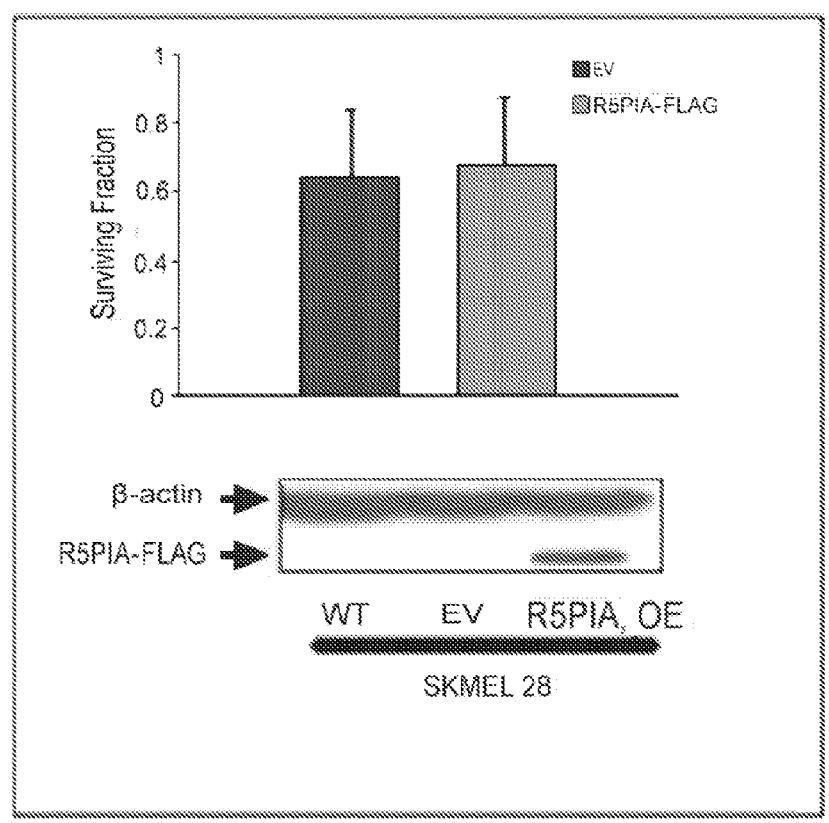
FIG. 7 shows the experimental outcome of knocking out R5PIA in SKMEL28 cells. (A) Cell survival rates are graphed based on total radiation exposure, and (B) a western blot of RGS-19 protein after siRNA transfection.

A multivariate linear regression model of gene expression and radiosensitivity (SF2) was developed in a 35 cell line database within the context of an accurate radiation sensitivity classifier. The clinical value of a radiosensitivity predictive model is significant, therefore understanding the intricacies of its operation were critical. The predictive algorithm identified five components of functional/biological relevance to the network that proved best at building the most accurate predictor, genes rbap48, top1, rgs19, r5pia and an unknown gene. FIG. 1 shows a schematic representation of the classifier algorithm. As shown in FIGS. 2-5, rbap48 and rgs-19 were biologically-validated as network components. Consistent with model predictions, depicted in FIG. 2, siRNA knockdown of rbap48 in HCT-116 cells, seen in FIG. 3(b), resulted in radioresistance as seen in FIG. 3(a). Next, G-protein signaling regulator rgs-19 was overexpressed in MDA-MB231 cell lines, seen in FIG. 5(b). Overexpression led to enhanced radiosensitization of the cell lines compared to EV-transfected controls, as seen in FIG. 5(a). This was consistent with model predictions, seen in FIG. 4. In contrast, overexpression of r5pia in MALME-3M melanoma cell lines, seen in FIG. 7(b), resulted in no radiophenotypic change, as seen in FIG. 7(a). This result was contrary to the predicted response, seen in FIG. 6. Finally, top-1 is a clinically validated radiosensitizing target in current clinical use, and confirmed that the linear regression model is reasonably accurate at identifying radiosensitivity network components.

The model was more fully developed to map the radiation sensitivity network by incorporating biological interactions with the genomic/SF2 database. A linear model was created for each gene in the cell line dataset. Common elements of radiation response were analyzed for variability introduced by multiple cell lines in the classifier to explicitly model the dynamic states. The dynamic states were models incorporating biological variables that have been reported to perturb the radiosensitivity network: tissue of origin (TO), ras status (mut/wt) and p53 status along with gene expression. The resulting model:

$$SF2 = k_0 + k_1(y_x) + k_2(TO) + k_3(\text{ras status}) + k_4(p53\text{ status}) + k_5(y_x)(TO) + k_6(y_x)(\text{ras status}) + k_7(TO)(\text{ras status}) + k_8(y_x)(p53\text{ status}) + k_9(TO)(p53) + k_{10}(\text{ras status})(p53\text{ status}) + k_{11}(y_x)(TO)(\text{ras status}) + k_{12}(y_x)(\text{ras status})(p53\text{ status}) + k_{13}(TO)(\text{ras status})(p53\text{status}) + k_{14}(y_x)(TO)(\text{ras status})(p53\text{ status})$$

represents 14 different potential dynamic states based on the four chosen variables and interactions between those variables. Original cell line data was created on HU6800 GeneChips while the newer patient data was created on HG-U133Plus Chips. The probesets were translated using a blast program to identify the best U133Plus probeset match to the consensus sequence from which the 6800 probeset was designed using Affymetrix software. The 500 genes identified with the smallest sum of squared residuals for the developed linear model were were further analyzed using Analysis of Variance (ANOVA) to determine the significant terms (e.g. gene, ras status) and correlation to SF2 across cell lines. The model produced four significant dynamic states in the radiosensitivity network, reduced from the 14 hypothetical states. TO and ras status and their interaction with gene expression proved to be key variables in defining the four states. Interestingly, the prostate cancer TO term grouped separately. In contrast p53 was not found to be a significant factor in the analysis. Cell lines grouped in the three states mainly distinguished by the presence of a mutated ras. The ras wt population was divided in two groups (NSCLC and Ovarian vs. Other TO). The ras term was dominant, therefore cell lines with mutated ras grouped closer than cell lines from the same TO, as exemplified by breast cancer cell lines (HS578T, MDAMB231) grouped together with other cell lines that shared this biological feature.

To explore the functional difference in the dynamic states, a pathway analysis was performed. GeneGO MetaCore identified a series of significant pathways shared by the 500 genes, depicted in FIGS. 8A-C. As seen in FIG. 9, key biological differences exist across dynamic states in the network. For example, dynamic state 2 represented pathways in metabolism, hypoxia and Akt, seen in FIGS. 10A-B. Dynamic state 3 represented 29 pathways, 11 of which were cell cycle related, seen in FIGS. 11A-C. Finally, dynamic state 4 was the most functionally diverse, representing pathways in DNA repair, cell cycle regulation, adhesion, apoptosis, immune response and protein kinase cascades, seen in FIGS. 12A-C. While many of these pathways have been implicated in the regulation of radiation response, the model evidences the importance of each pathway's dependence on the biological context that defines the dynamics of the network.

Figure 13:
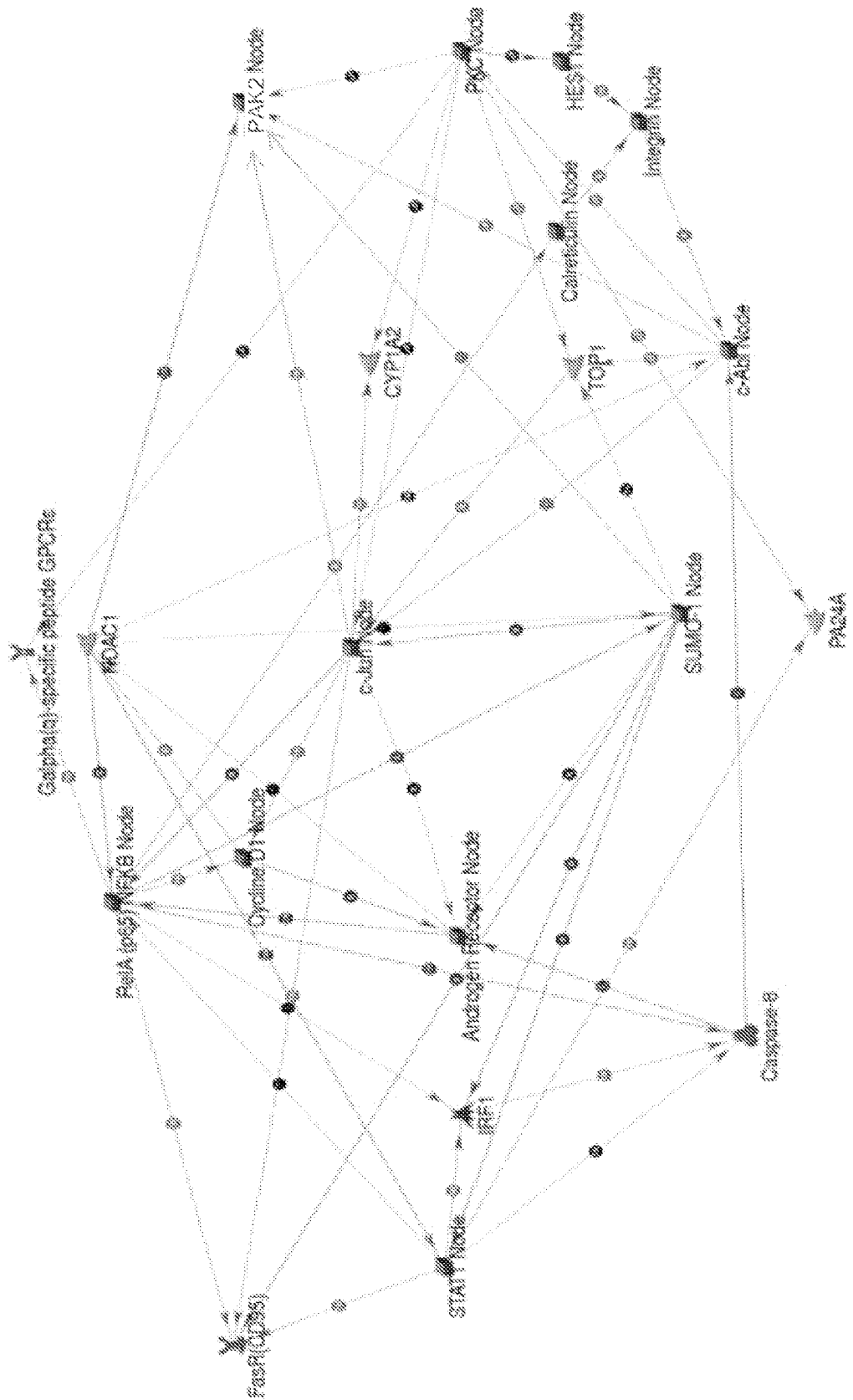
FIG. 13 is an illustration showing the network model of the radiation response. The topology of major hubs is shown.

To visualize the network proposed by the mathematical model, the primary interconnections of the original 500 genes selected using literature-based annotations were plotted using GeneGO, seen in FIG. 13. The gene probesets were loaded into GeneGO MetaCore and analyzed for overexpression in various cellular pathways defined by the dynamic states, seen in FIG. 14. Hubs were defined within the gene network as a node consisting of at least 5 connections to other genes, seen in FIG. 15. All hubs with more than 5 connections and less than 50% of edges hidden within the network were chosen as the major hubs for classification purposes. This network model, shown in FIG. 13, proposes ten central hubs: c-jun, HDAC-1, RelA (p65 subunit of NFKB), PKC, SUMO-1, c-Abl, STAT-1, AR, PAK2 and IRF1, seen in FIG. 15. Remarkably, each of these hubs is reportedly involved in radiation signaling and 6/10 (HDAC1, NF-KB, c-ABL, STAT1, AR, SUMO-1) have been proposed as targets for radiosensitizer development. Additionally, the model proposes significant cross-talk among the central hubs, consistent with a robust system with significant signal redundancy. It should be noted that these hubs would not be identified using the correlation of gene expression to SF2 as the median $R^2$ of these hubs is 0.02.

Because the hub classifier was applied to datasets generated from differing GeneChip platform and technology, genes were normalized using a rank-based approach. Gene expression was ranked for each gene per sample using the identified ten hubs.

The model was analyzed by testing the effect of c-jun knockdown on radiosensitivity, thereby determining whether biologically-relevant network dynamics and interactions were being captured. Selection of c-jun was due to the fact that c-jun is a central hub and an AP-1 regulated pathway was the only commonality between the three main dynamic states. Importantly, c-jun has been shown to play a role as an early response gene in the initial stages of radiation response. The model predicted c-jun knockdown would cause differing results, based on the biological context as defined by TO. The predictions and experimental outcomes, using a linear fit for c-jun gene expression to SF2 stratified by TO, are shown in FIG. 16. As seen in FIG. 17, c-jun siRNA was transfected into 8 different cell lines, representing the three tissues types selected: NSCLC, colon and breast. Downregulation of c-jun resulted in induction of radiation resistance in NSCLC cell lines, consistent with the linear regression curve derived from the model. Cell survival curves in both A549 and H460 cell lines confirmed these observations. Furthermore, the radiophenotype of colon cancer cell lines (when considered as a group) was unaffected by c-jun downregulation, also supporting the model. However, it should be noted that in HCT-116 cells, c-jun downregulation led to radioresistance (p=0.52). Additionally, radiation response in breast cancer cell lines was unchanged by c-jun siRNA transfection, while the linear model predicted radiosensitization. The model was experimentally validated in two of three tested instances, for lung cancer (radioresistance, p=0.005) and colon cancer (no change).

Figure 18:
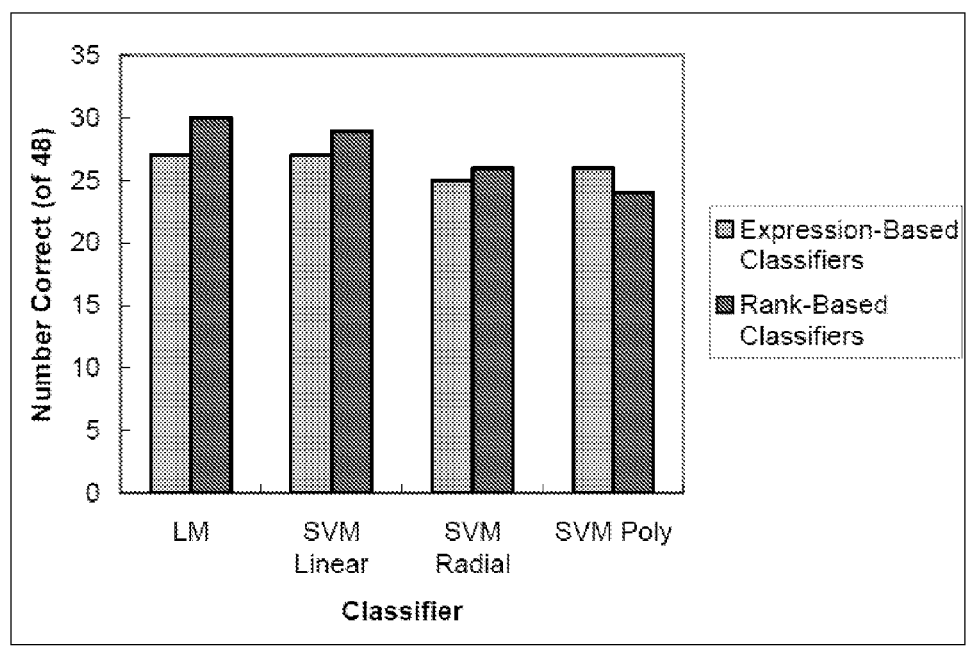
FIG. 18 is a graph showing leave-one-out cross-validation results for hub-based classifier on dataset cell lines.

The experiments supported the model's ability to capture the influence of biological context on network outcome. However, because radiosensitivity prediction is linked to biological contexts, predicitive features changed depending on expression context. A hub-based gene expression classifier was built to estimate the predictive accuracy of the network model. A linear regression model was developed along with support-vector machines for comparison, however, the linear regression model found the most accurate at $30/48$ (62.5%), seen in FIG. 18. Further, the rank-based dataset normalization yielded a more accurate classifier than using actual gene expression values, shown in FIG. 19.

Figure 20:
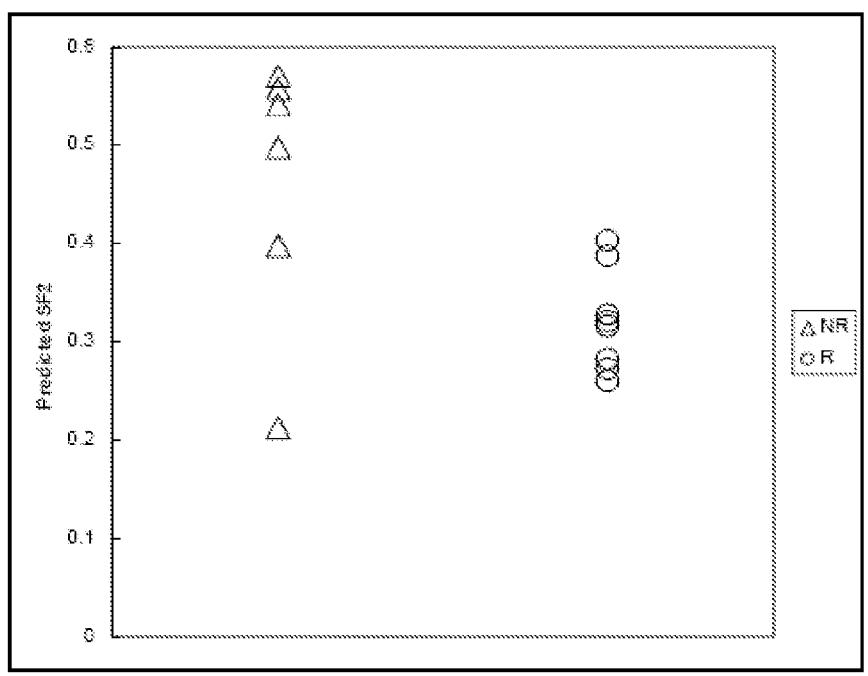
FIG. 20 shows topotecan radiation sensitivity predictions and results for rectal cancer patients. (A) A table of rectal cancer samples shows the radiation sensitivity using survival fractions and clinical response, and (B) a graph of predicted outcomes of rectal cancer radiotherapy, as defined by the network model.
Figure 21:
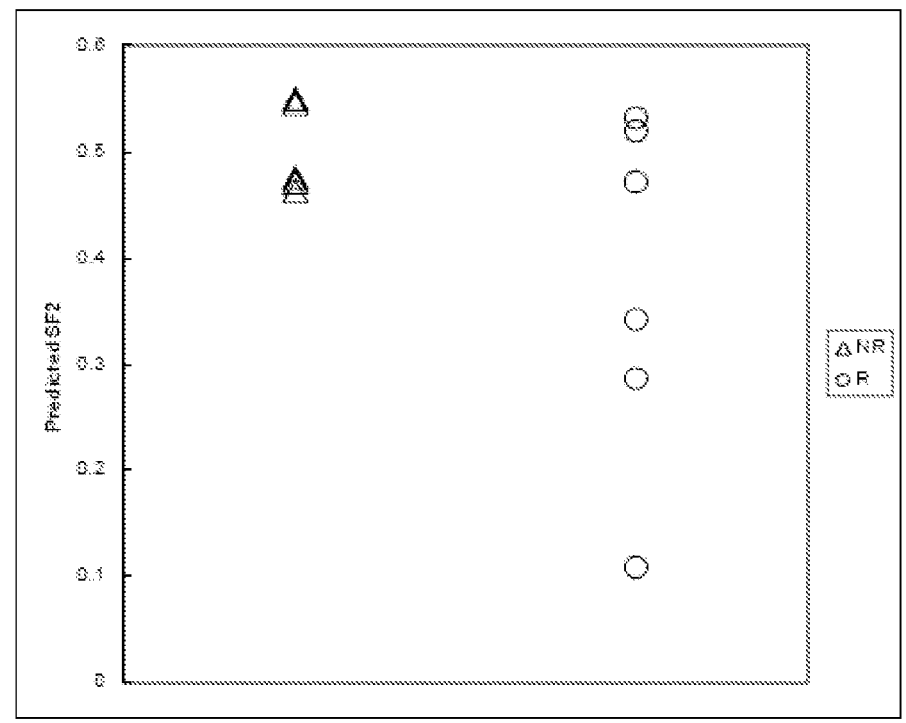
FIG. 21 shows radiation sensitivity predictions and results for esophageal cancer patients. (A) A table of rectal cancer samples shows the radiation sensitivity using survival fractions and clinical response, and (B) a graph of predicted outcomes of esophageal cancer radiotherapy, as defined by the network model.
Figure 22:
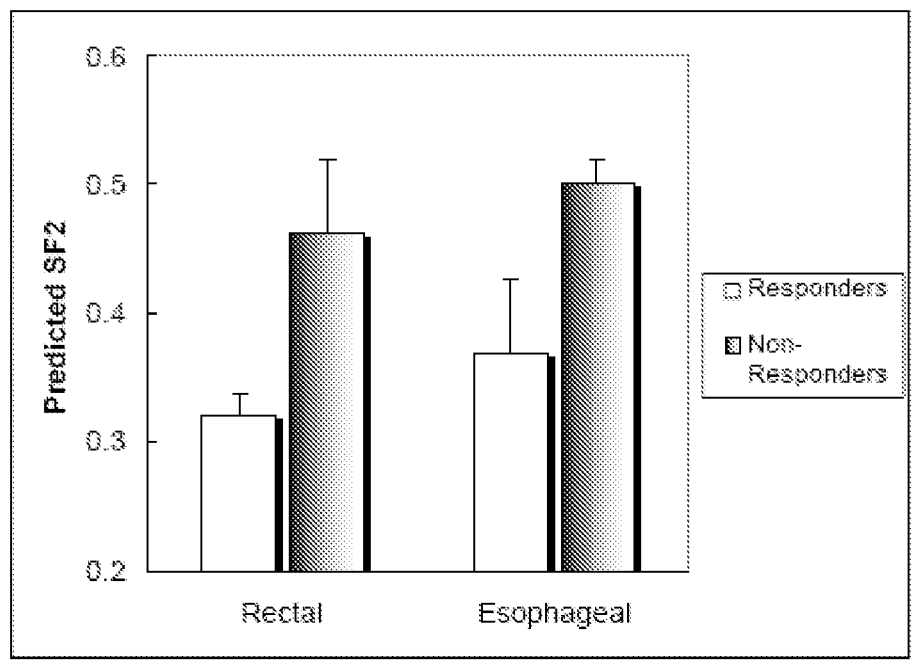
FIG. 22 is a graph showing a summary of predicted responses for both rectal and esophageal cancer radiosensitivity. As seen, the model noted significant radiation sensitivity response between responders and non-responders.
Figure 23:
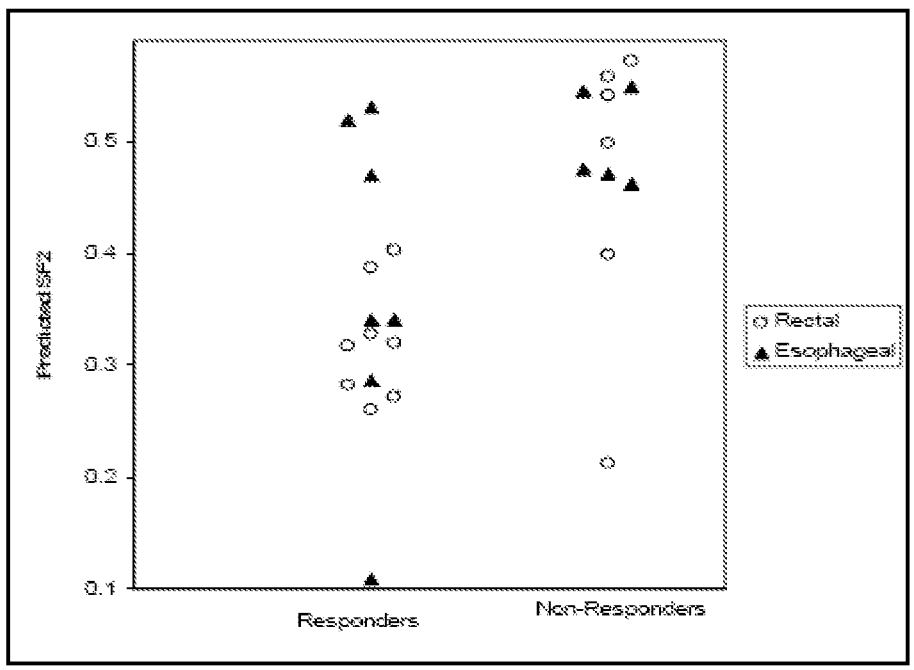
FIG. 23 is a graph showing the summary of experimental data from rectal and esophageal cancer radiosensitivity.

To determine the clinical relevance of the model, it was used to predict clinical response in 14 patients with locally-advanced rectal cancer treated with preoperative concurrent radiochemotherapy. Pre-treatment samples from the patients were arrayed on the HG-U133Plus platform. The tumors were staged at initial biopsy with ultrasound and later stages using pathological information from surgical resection. Downstaging in the T stage from the TNM staging system translated R (response) in the dataset, while no change or progressive disease was recorded as NR (no response). Data was processed using gcRMA using the Bioconductor implementation. Gene expression values for the 10 hubs were converted to ranks and SF2 values were generated from the model created using cell line data, depicted in FIG. 20 (mean predicted SF2 R vs. NR 0.31 vs 0.45, p=0.03). Responders were further tested for significantly lower predicted SF2 using a one sided Wilcoxon rank-sum test (P=0.02964). The 10 gene model was further tested in a cohort of 12 patients with esophageal cancer also treated with preoperative radiochemotherapy. A pre-treatment biopsy was collected from the patients and tissue arrayed on the HG-U133Plus platform. The entire dataset was processed (22 patient samples), though only 12 esophageal cancer samples with chemoradiation response were available. Chips were normalized using RMA in the GENE implementation (Eschrich, 2007). Gene expression values for the ten hubs were converted to rank values and the SF2 values were generated from the model created using cell line data. Similar to the rectal cancer cohort, responders were predicted to be more radiosensitive than non-responders as determined by predicted SF2, seen in FIG. 21 (0.34 vs. 0.48, p=0.05). For both patient cohorts, rectal and esophageal cancer, the model predictions significantly separated pathological responders (R) from non-responders (NR), seen in FIGS. 22 and 23. A test of significantly lower predicted SF2 values in the CR group was performed using a one-sided Wilcoxon rank-sum test (P=0.05303). These results are encouraging since no esophageal cancer cell lines were included in the original database, suggesting that the model is capturing central common aspects of the radiosensitivity network that are of clinical relevance.

The model was further analyzed against ten known radiosensitizer drug targets, both in clinical development or routine clinical use. All drug targets are linked by primary interconnection to at least one central hub of the model, seen in FIG. 24, supporting the clinical relevance of the radiosensity network model. Moreover, the model revealed that the targets interference with only a minority of the hubs, suggesting the current clinical approach to radiosensitization is inefficient at disrupting the radiosensitivity network.

A fundamental objective of the field of systems biology is to develop an understanding of the dynamics and structure of complex biological systems. The presented model integrates both of these elements and represents an important advance in the understanding of the radiation response regulatory network.

The mathematical model proposes a highly interconnected network topology with ten central hubs and significant signal redundancy. The redundancy explains why targeting a single hub could lead to different or inconsistent system outputs (i.e c-jun knockout), as phenotypic responses may be driven by competing signal networks. The complex combination of signals is consistent with the continuous nature of radiation response, providing a framework to explain individual response variability. The hubs identified by the model have been shown important in the regulation of radioresponse. All targets connected via at least one of hub, supporting the biological validity of the model. In contrast, 20 alternative networks were developed using chance for feature selection. The mathematical model outperformed all alternative chance networks in all instances, when target connectivity and hub's relevance in radioresponse were used as benchmarks for comparison.

An advantage of the mathematical model is that it considers the inherent individual variability that exists in the response to therapeutic agents. Furthermore, biological variables that may define specific resistance/sensitivity phenotypes can be included, allowing the model to capture several signaling states in the network. This last concept has been proposed to explain the lack of commonality between validated disease-specific molecular signatures in clinical oncology. The model can identify novel network components and integrate complex interactions and dynamics into biological predictions. Finally, it provides a network architecture that allows hypothesis development, extending from basic radiation molecular biology to hypothesis with a direct impact in clinical radiation oncology.

Material and Methods

Cell lines—Cell lines were obtained directly from the National Cancer Institute (NCI). Cells were cultured in RPMI 1640 media supplemented with glutamine (2 mM), antibiotics (penicillin/streptomycin, 10 U/ml) and Heat inactivated Fetal Bovine Serum (10%) at 37° C. with an atmosphere of 5% $CO_2$.

Radiation Survival Assays (SF2)—The SF2 of cell lines used in the classifier were obtained from the literature in 23 of the 48 cell lines in our analysis. For cell lines obtained from the literature, papers (published before 2004) were used that reported on clonogenic assays that had been performed without the use of any substrate (i.e. agar) and that required cells to be in log phase at the time of irradiation. The cell lines also needed at least two reported values in the literature by different laboratories. Mean SF2 values were determined for each cell line and used for the generation of the model. The remaining 25 cell lines (MCF-7, MDA-MB-435, KM-12, HOP62, H23, BT549, MDA-MB-231, HCT116, HT29, H460, OVCAR5 and PC3) SF2 values were determined in the lab. Clonogenic survival assays after 2 Gy of radiation were performed as previously described (J. Staunton, D. Slonim, Chemosensitivity Prediction by Transcriptional Profiling, Proc. Nat. Acad. Sci., 98:19, 10787-10792). Plating efficiency for each cell line was determined, prior to SF2 determination. Cells were plated so that 50-100 colonies would form per plate and incubated overnight at 37° C. overnight to allow for adherence. Cells were then radiated with 2 Gy using a Cesium Irradiator (J. L Sheperd, Model I 68A, San Fernando, Calif.). Exposure time was adjusted for decay every three months. After irradiation cells were incubated for 10-14 days at 37° C. before being stained with crystal violet.

Only colonies with at least 50 cells were counted. SF2 was determined by the following formula:

SF2=number of colonies/total number of cells plated× plating efficiency.

Microarrays—Gene expression profiles were from Affymetrix HU6800 chips (7,129 genes) or from a previously published study (J. Torres-Roca, S. Eschrich, et al., Prediction of Radiation Sensitivity Using a Gene Expression Classifier, Cancer Res., 65:16, 7169-7176). The gene expression data had been previously preprocessed using the Affymetrix MAS 4.0 algorithm in average difference units. Negative expression values were set to zero and the chips were normalized to the same mean intensity.

siRNA transfection. $3\times10^5$ Hs-RbAp48-hi cells in 2 mL antibiotic-free complete medium were plated in each well of a six-well plate and after 24 h of incubation were transfected following the basic dharmaFECT transfection protocol (Dharmacon, Inc., Lafayette, Colo.) with either a pool of 4 negative control siRNAs (siRNA pool) or RbAp48 siRNA designed by Dharmacon's SMARTpool technology both at 100 nM final concentration. 48 hours after transfection, cells were lysed for Western blotting, to confirm the knockdown of RbAp48, or plated in coverslips for immunofluorescence.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. A method of predicting a clinical response to anticancer radiation therapy in a patient with rectal cancer, the method comprising:
    obtaining a sample of target cells from the patient;
    determining genomic expression levels of c-jun, HDAC-1, RelA, PKC, SUMO-1, c-Abl, STAT-1, AR, PAK2, and IRF1 in the sample; and
    applying the genomic expression levels of c-jun, HDAC-1, RelA, PKC, SUMO-1, c-Abl, STAT-1, AR, PAK2, and IRF1 in the sample to a multivariate linear regression model of treatment sensitivity, whereby a high expression value correlates with a treatment-sensitive phenotype thereby predicting the clinical response to anticancer radiation therapy.

2. The method of claim 1, wherein the sample of target cells comprises rectal cancer cells.

3. The method of claim 1, wherein the multivariate linear regression model is created comprising the steps of:
    developing a multivariate linear regression model of radiosensitivity and gene expression comprising:
    establishing the radiation sensitivity of at least one cell line; and
    determining genomic expression levels of c-jun, HDAC-1, RelA, PKC, SUMO-1, c-Abl, STAT-1, AR, PAK2, and IRF1 in the at least one cell line; and
    incorporating biological interactions of common radiation response elements with the radiosensitivity network components.

4. The method of claim 3, wherein genomic expression levels in the at least one cell line are determined from a microarray.

5. The method of claim 3, wherein the common radiation response elements are selected from the group consisting of: tissue origin, ras mutation status, p53 status, tissue origin interaction with gene expression, ras mutation status interaction with gene expression, and p53 status interaction with gene expression.

6. The method of claim 1, wherein the model is a rank-based linear regression model.

7. A method of predicting a clinical response to anticancer radiation therapy in a patient with esophageal cancer, the method comprising:
    obtaining a sample of target cells from the patient;
    determining genomic expression levels of c-jun, HDAC-1, RelA, PKC, SUMO-1, c-Abl, STAT-1, AR, PAK2, and IRF1 in the sample; and
    applying the genomic expression levels of c-jun, HDAC-1, RelA, PKC, SUMO-1, c-Abl, STAT-1, AR, PAK2, and IRF1 in the sample to a multivariate linear regression model of treatment sensitivity, whereby a high expression value correlates with a treatment-sensitive phenotype thereby predicting the clinical response to anticancer radiation therapy.

8. The method of claim 7, wherein the sample of target cells comprises esophageal cancer cells.

9. The method of claim 7, wherein the multivariate linear regression model is created comprising the steps of:
    developing a multivariate linear regression model of radiosensitivity and gene expression comprising:
    establishing the radiation sensitivity of at least one cell line; and
    determining genomic expression levels of c-jun, HDAC-1, RelA, PKC, SUMO-1, c-Abl, STAT-1, AR, PAK2, and IRF1 in the at least one cell line; and
    incorporating biological interactions of common radiation response elements with the radiosensitivity network components.

10. The method of claim 9, wherein genomic expression levels in the at least one cell line are determined from a microarray.

11. The method of claim 9, wherein the common radiation response elements are selected from the group consisting of: tissue origin, ras mutation status, p53 status, tissue origin interaction with gene expression, ras mutation status interaction with gene expression, and p53 status interaction with gene expression.

12. The method of claim 7, wherein the model is a rank-based linear regression model.

* * * * *

UNITED STATES PATENT AND TRADEMARK OFFICE
CERTIFICATE OF CORRECTION

PATENT NO. : 8,655,598 B2
APPLICATION NO. : 13/037156
DATED : February 18, 2014
INVENTOR(S) : Javier F. Torres-Roca et al.

It is certified that error appears in the above-identified patent and that said Letters Patent is hereby corrected as shown below:

In the Specification

Column 1, Line 16 through Line 20 should read:
STATEMENT OF GOVERNMENT INTEREST
This invention was made with government support under grant number CA108926 awarded by the National Institutes of Health and grant number DAMD17-02-2-0051 awarded by the US Army Medical Research and Materiel Command (ARMY/MRMC). The Government has certain rights in the invention.

Signed and Sealed this
Thirteenth Day of August, 2019

Andrei Iancu
*Director of the United States Patent and Trademark Office*